US009682184B2

(12) United States Patent
Wong

(10) Patent No.: US 9,682,184 B2
(45) Date of Patent: Jun. 20, 2017

(54) MATERIALS FOR REMOVAL OF TOXINS IN SORBENT DIALYSIS AND METHODS AND SYSTEMS USING SAME

(71) Applicant: Fresenius Medical Care Holdings, Inc., Waltham, MA (US)

(72) Inventor: Raymond J. Wong, Norman, OK (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 358 days.

(21) Appl. No.: 14/361,045

(22) PCT Filed: Dec. 27, 2012

(86) PCT No.: PCT/US2012/071740
§ 371 (c)(1),
(2) Date: May 28, 2014

(87) PCT Pub. No.: WO2013/101888
PCT Pub. Date: Jul. 4, 2013

(65) Prior Publication Data
US 2014/0336568 A1 Nov. 13, 2014

Related U.S. Application Data

(60) Provisional application No. 61/581,153, filed on Dec. 29, 2011.

(51) Int. Cl.
*B01J 20/28* (2006.01)
*B01J 20/02* (2006.01)
(Continued)

(52) U.S. Cl.
CPC ........ *A61M 1/1696* (2013.01); *A61M 1/1656* (2013.01); *A61M 1/287* (2013.01);
(Continued)

(58) Field of Classification Search
None
See application file for complete search history.

(56) References Cited

U.S. PATENT DOCUMENTS 3,726,803 A * 4/1973 Bayless ................. B01J 13/206
252/62.54
4,081,402 A * 3/1978 Levy ................... A61M 1/3679
428/36.4

(Continued)

FOREIGN PATENT DOCUMENTS

WO 2009157877 A1 12/2009

OTHER PUBLICATIONS

International Search Report and Written Opinion of the International Searching Authority issued in corresponding International Patent Application No. PCT/US2012/071740 dated Mar. 18, 2013 (10 pages).

Primary Examiner — Krishnan S Menon
Assistant Examiner — Bradley R Spies
(74) *Attorney, Agent, or Firm* — Kilyk & Bowersox, P.L.L.C.

(57) ABSTRACT

A sorbent dialysis cartridge is provided for removal of uremic toxins from dialysate wherein the sorbent cartridges can use non-enzymatic urea-binding materials in place of urease. The cartridge can have a first sorbent layer loaded with a polymerizable urea complexing agent and a second sorbent layer loaded with a crosslinker. The crosslinker can be crosslinkable with a soluble urea complex reaction product of the polymerizable urea complexing agent and urea when passing through the first sorbent layer to form a crosslinked polymeric urea complex which is attachable to the second sorbent layer. In another option, a sorbent layer can be used which has an insolubilized crosslinked polymeric urea-bindable complex attached thereto, wherein the crosslinked polymeric urea-bindable complex can be a reac- (Continued)

tion product of a crosslinker and polymerizable urea complexing agent. Methods and sorbent dialysis systems using the cartridge, and methods of making the sorbent material, are provided.

19 Claims, 9 Drawing Sheets

(51) Int. Cl.
    *B01J 20/22* (2006.01)
    *A61M 1/16* (2006.01)
    *A61M 1/28* (2006.01)
    *B01J 20/30* (2006.01)
    *B01J 20/06* (2006.01)
    *B01J 20/20* (2006.01)

(52) U.S. Cl.
    CPC .......... *B01J 20/0211* (2013.01); *B01J 20/06* (2013.01); *B01J 20/20* (2013.01); *B01J 20/223* (2013.01); *B01J 20/28052* (2013.01); *B01J 20/3071* (2013.01)

(56) References Cited

U.S. PATENT DOCUMENTS

| | | | |
|---|---|---|---|
| 4,176,090 A * | 11/1979 | Vaughan | B01J 20/12 423/328.2 |
| 4,216,188 A * | 8/1980 | Shabtai | B01J 20/12 423/328.2 |
| 4,980,332 A * | 12/1990 | Schramm | B01J 29/049 252/1 |
| 6,627,164 B1 | 9/2003 | Wong | |
| 6,818,196 B2 | 11/2004 | Wong | |
| 7,033,498 B2 | 4/2006 | Wong | |
| 7,101,519 B2 | 9/2006 | Wong | |
| 7,566,432 B2 | 7/2009 | Wong | |
| 7,736,507 B2 | 6/2010 | Wong | |
| 7,906,093 B2 | 3/2011 | Wong | |
| 8,409,444 B2 | 4/2013 | Wong | |
| 8,640,887 B2 | 2/2014 | Wong | |
| 8,647,506 B2 | 2/2014 | Wong | |
| 2010/0004588 A1 | 1/2010 | Yeh et al. | |
| 2010/0078387 A1* | 4/2010 | Wong | A61M 1/1696 210/656 |
| 2012/0234762 A1 | 9/2012 | Wong | |
| 2013/0190168 A1 | 7/2013 | Wong et al. | |
| 2014/0069858 A1 | 3/2014 | Wong | |

* cited by examiner

MATERIALS FOR REMOVAL OF TOXINS IN SORBENT DIALYSIS AND METHODS AND SYSTEMS USING SAME

This application is a National Stage Application of PCT/US2012/071740, filed Dec. 27, 2012, which claims the benefit under 35 U.S.C. §119(e) of prior U.S. Provisional Patent Application No. 61/581,153, filed Dec. 29, 2011, which is incorporated in its entirety by reference herein.

FIELD OF THE INVENTION

The present invention generally relates to the field of sorbent dialysis, and more specifically to a sorbent cartridge with non-enzymatic urea binders, and a method and a system using the cartridge in sorbent dialysis.

BACKGROUND OF THE INVENTION

Kidney failure can cause accumulation in body fluids, such as blood, of toxins and derivatives and metabolites of organic drugs taken by the patient. Sorbent dialysis systems provide treatment for patients with acute or chronic kidney disease. Dialysate is delivered to a dialyzer in prescribed amounts to cleanse the blood of impurities, correct the patient's body chemistry, and remove excess fluid. In sorbent dialysis, a sorbent cartridge can purify the initial dialysate and continuously regenerate spent dialysate throughout the treatment. This can significantly reduce the volume of dialysate needed for dialysis. Closed loop multi-pass sorbent based dialysis systems, for example, regenerate dialysate for reuse by passing spent dialysate through a regeneration section comprising at least one sorbent cartridge and suitable additives. Spent dialysate comprising urea, which is diffused from impure blood in the dialyzer, passes through conventional sorbent cartridges. The sorbent cartridges bind uremic wastes, and also can be used for other tasks, such as balancing dialysate pH. A typical sorbent cartridge system can include, for example, an activated charcoal layer (a purification layer), a urease enzyme layer (a conversion layer), a cation exchange layer, and an anion exchange layer. The REDY™ (REgenerative DialYsis) System is an example of a commercially available sorbent cartridge system which incorporates such an arrangement of filtration and sorbent materials. During regenerative dialysis, the used or spent dialysate can move up through the layers of the cartridge and a high purity regenerated dialysate can emerge from the cartridge outlet for recirculation to the dialyzer. The activated charcoal or carbon layer can be used to absorb organic metabolites such as creatinine, uric acid, and nitrogenous metabolic waste of the patient as well as chlorine and chloramines from the water. Urease used in the urease layer can be an enzyme that catalyzes the hydrolysis of urea into carbon dioxide and ammonia. Ammonium carbonate is released by a urease layer in a conventional sorbent cartridge. Ammonium created in the urease layer can be removed in the cation exchange layer, e.g., an adsorbent zirconium phosphate, in exchange for release of $Na^+$ and $H^+$ ions. The carbonate from the urea hydrolysis then can combine with $H^+$ to form bicarbonate ($HCO_3^-$) and carbonic acid ($H_2CO_3$). Carbonic acid is an unstable organic acid; most of it rapidly breaks down into water and carbon dioxide molecules ($CO_2$). The anion exchange layer, e.g., HZO containing acetate as a counter ion, can remove $HCO_3^-$, $P^-$, and other anions (e.g., $F^-$ in water), and releases acetate. The $CO_2$ gas bubbles are vented from the cartridge.

The present investigators have recognized that conventional sorbent dialysis using an immobilized urease layer in the sorbent cartridge can have disadvantages, such as needing a significant volume of water in the dialysate, ammonia leakage and monitoring requirements, variations of Na and bicarbonate in dialysate, high $PCO_2$ in dialysate, acetate and soluble Al and Zr leakages, concanavalin from Jack Bean meal, bacterial and endotoxin removal needs, high pressure problems, insufficient regenerated dialysate quality, and the need for the immobilized urease layer itself. The present investigators have specifically recognized that conventional sorbent dialysis using an immobilized urease layer may require upwards to about 6 liters water in the dialysate to minimize variation of sodium ($Na^+$) and bicarbonate ions ($HCO_3^-$) caused by interaction of the enzymatic hydrolysis products of urea (e.g., ammonia carbonate as ammonium ($NH_4^+$) and carbonate ($CO_3^{-2}$)) in dialysate with zirconium sorbent (e.g., ZrP), which adsorbs ammonia in exchange for release of sodium and hydrogen ions from the sorbent material. The present investigators further have recognized that it would desirable to eliminate the foregoing disadvantages while simultaneously providing sorbent dialysis which is effective to regenerate spent dialysate or purify dialysate or water to make up dialysate by removing uremic toxins therefrom with non-enzymatic urea binders.

SUMMARY OF THE INVENTION

A feature of the present invention is to provide a sorbent cartridge with non-enzymatic urea binders which are useful for detoxifying spent dialysate containing uremic toxins.

Another feature of the present invention is to provide a method to detoxify spent dialysate with a sorbent cartridge that does not need to contain a urease layer to provide purified or regenerated dialysate.

A further feature of the present invention is to provide a dialysis system for conducting dialysis comprising a dialyzer in fluid communication with a sorbent cartridge containing a non-enzymatic urea binder, wherein uremic toxins in spent dialysate can be converted to more highly adsorbable complex forms for removal without generation of ammonia and with reduced water volume requirements before recirculating the resulting regenerated dialysate back to the dialyzer.

Additional features and advantages of the present invention will be set forth in part in the description that follows, and in part will be apparent from the description, or may be learned by practice of the present invention. The objectives and other advantages of the present invention will be realized and attained by means of the elements and combinations particularly pointed out in the description and appended claims.

To achieve these and other advantages, and in accordance with the purposes of the present invention, as embodied and broadly described herein, the present invention relates in part to a sorbent cartridge comprising sorbent (a) and/or (b). Sorbent (a) has a first sorbent layer loaded with a polymerizable urea complexing agent and a second sorbent layer loaded with a crosslinker. The crosslinker is crosslinkable with a soluble urea complex reaction product of the polymerizable urea complexing agent and urea when passing through the first sorbent layer to form a crosslinked polymeric urea complex which is attachable to the second sorbent layer (or one or more components of the second sorbent layer). Sorbent (b) has a sorbent layer comprising an insolubilized crosslinked polymeric urea-bindable complex attached thereto. The crosslinked polymeric urea-bindable complex comprises a reaction product of a crosslinker and polymerizable urea complexing agent.

The present invention is further directed to a method to regenerate or purify spent dialysate comprising passing the spent dialysate through the indicated sorbent cartridge.

The present invention is further directed to a method of preparing purified fresh dialysate for dialysis comprising passing fresh dialysate through the indicated sorbent cartridge.

The present invention is further directed to a method of regenerating or purifying spent dialysate by a process which has options (a) and/or (b). Process (a) includes (i) passing urea-containing dialysate through a first sorbent layer loaded with a polymerizable urea complexing agent to form a soluble urea complex, for instance, at a pH of about 2 or less, and (ii) passing the soluble urea complex through a second sorbent layer loaded with a crosslinker which crosslinks with the soluble urea complex to form a crosslinked polymeric urea complex which is attached to the second sorbent layer (or one or more components of the second sorbent layer). Process (b) includes (i) reacting a crosslinker loaded on a sorbent layer with a polymerizable urea complexing agent to form an insolubilized crosslinked polymeric urea-bindable complex attached to the sorbent layer, and (ii) passing urea-containing dialysate through the sorbent layer having the insolubilized crosslinked polymeric urea-bindable complex attached thereto to complex urea therewith, for instance, at a pH of about 2 or less.

The present invention is further directed to an apparatus for conducting dialysis comprising the indicated sorbent cartridge and a dialyzer in fluid communication with the sorbent cartridge, wherein spent dialysate passes from the dialyzer to and through the sorbent cartridge before recirculation of the regenerated dialysate back to the dialyzer for reuse.

The present invention is further directed to a dialysis system comprising the indicated sorbent cartridge and a source of spent dialysate, such as a dialyzer, wherein the source of the spent dialysate is in fluid communication with the sorbent cartridge and the spent dialysate passes to and through the sorbent cartridge before recirculation of the regenerated dialysate for reuse.

The present invention is further directed to a method of making urea-binding carbon for sorbent devices, comprising a) combining glyoxal and zirconium ion source solution to provide a glyoxal/zirconium solution; b) immersing activated carbon in the glyoxal/zirconium solution including added acid to provide treated activated carbon; c) separating solution from the treated activated carbon; d) acid washing the treated activated carbon to provide acid-washed treated activated carbon; and e) drying the acid-washed treated activated carbon to provide a urea-binding carbon product. The present invention also relates to a urea-binding carbon product of the indicated process.

It is to be understood that both the foregoing general description and the following detailed description are exemplary and explanatory only and are only intended to provide a further explanation of the present invention, as claimed.

The accompanying drawings, which are incorporated in and constitute a part of this application, illustrate some of the features of the present invention and together with the description, serve to explain one or more principles of the present invention. The drawings are not necessarily drawn to scale. Like numerals in the drawings refer to like elements in the various views.

DETAILED DESCRIPTION OF THE PRESENT INVENTION

Figure 1:
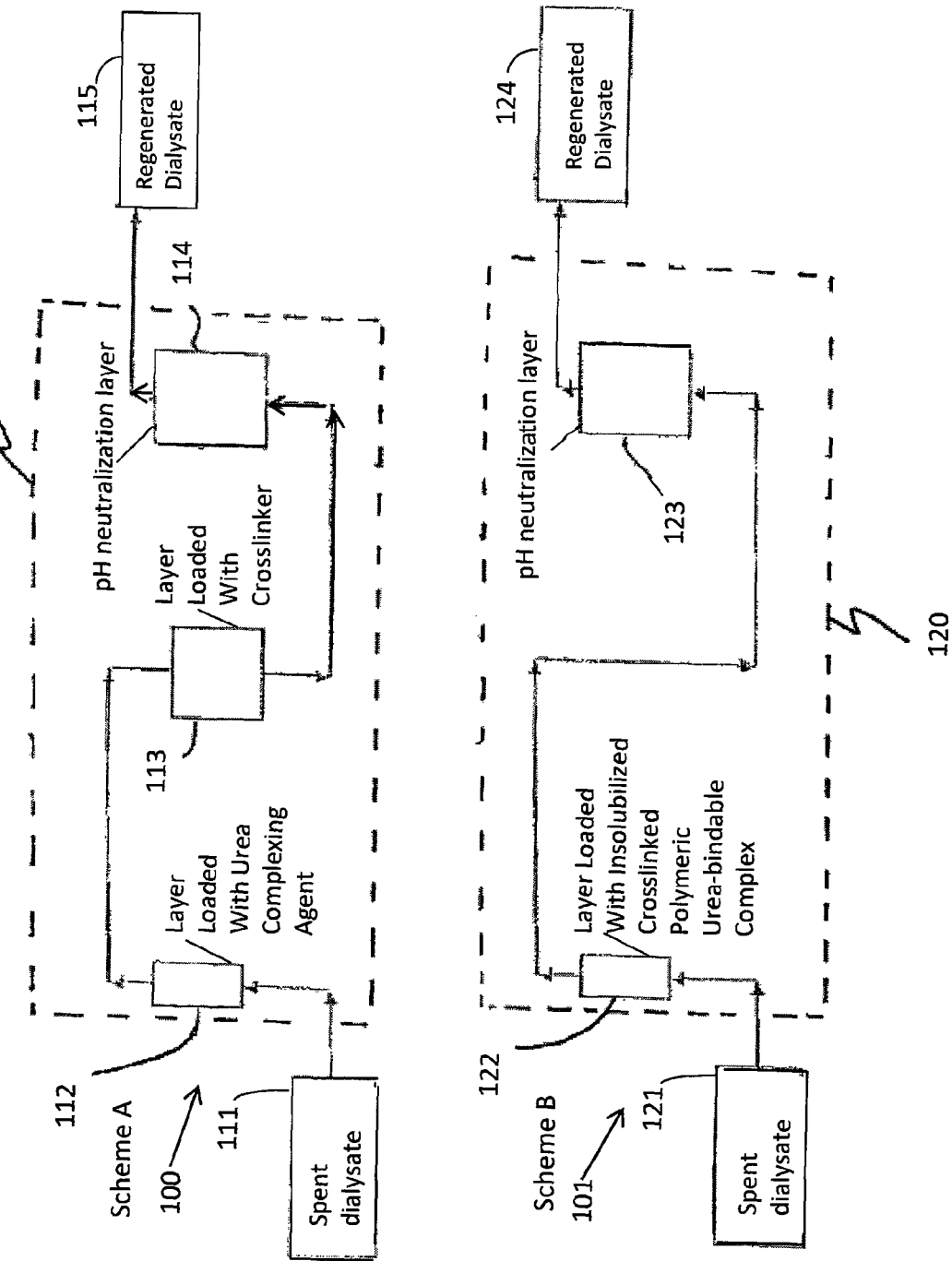
FIG. 1 shows process flow diagrams of sorbent dialysis methods according to Schemes A and B of examples of the present invention.

The present invention relates to materials useful for the removal of waste products and excess fluid that accumulates in dialysate fluids. These materials can be present in a container (e.g., one or more sorbent cartridges) capable of holding the materials useful for the removal process. The materials described in detail below, or the arrangement of materials, can be used in a dialysis system or other similar type of system that is useful for the removal of waste products and/or excess fluid that accumulates in dialysate fluids, for instance, as a result of conducting hemodialysis or peritoneal dialysis. As described in more detail below, the present invention is useful in purifying or regenerating dialysate used in hemodialysis and in peritoneal dialysis. Conventional dialysis solutions for peritoneal dialysis or hemodialysis can be used and regenerated by the present invention and are known to those skilled in the art.

The present invention, in part, relates to providing removal of uremic toxins from a patient by sorbent dialysis with non-enzymatic urea-binding sorbent materials. In the present invention, a non-enzymatic sorbent material can be converted into a direct urea binder which can be used in a sorbent cartridge(s) for dialysate regeneration or purification in sorbent dialysis. The sorbent cartridge(s) can be used for treatment of uremia and/or other conditions. The sorbent cartridge of the present invention can reduce or avoid generation of ammonia during urea removal because of the absence of enzymatic hydrolysis reactions of urea that are related to conventional use of urease. The environment of sorbent cartridges of the present invention thus can be stabilized and more uniform, such as with respect to sodium bicarbonate ionic concentrations and pH, during the urea removal reactions provided on the non-enzymatic urea-binding sorbent materials of sorbent cartridges of the present invention. This effect can permit, for example, a reduction in the volume of water required in recirculating dialysate in a dialysis system. In addition to removal of urea, the sorbent cartridge design of the present invention can improve sorbent dialysis quality by producing regenerated dialysate with ultrapure water quality by removal of bacteria, endotoxins, and/or by improved adsorption of organic solutes (e.g., drug removal such as phenol, barbiturates), toxic anions (e.g., carboxylates such as citrate, oxalate, phosphate, sulfate), and/or protein-bound toxins over conventional sorbent cartridges. These enhancements of the present invention can assist in economizing sorbent dialysis treatment.

In the present invention, the immobilization of non-enzymatic complexing agents, such as polyaldehydes, by cross-linkers on sorbents can make the sorbents active toward urea adsorption to provide adequate urea binding capacity which can eliminate the need for an immobilized urease layer or similar-acting enzyme in the sorbent cartridge. For purposes herein, a cartridge "free of an immobilized urease layer" refers to the absence in the cartridge or column of any stationary continuous layer of urease extending across an internal cross-section thereof that is available for fluid flow. Further, the cartridge or column of the present invention can be substantially free or completely free of any active urease in the fluid flow compartment of the cartridge. For example, the total content of active urease in the fluid flow compartment of the cartridge can be less than about 5 wt %, or less than about 3 wt %, or less than about 2 wt %, or less than about 1 wt %, or less than about 0.5 wt %, or less than 0.1 wt %, or from 0 to about 5 wt %, or other values within these ranges, based on the total immobilized weight portion of the cartridge contents. The degree of activity provided in the non-enzymatic urea-binding sorbent can be dependent on the type of urea complexing agent and pH.

The urea complexing agent used in sorbent cartridges of the present invention can be applied to removal of uremic toxins from dialysate, for example, in a two-stage urea binding format or a single-stage urea binding format. In a two-stage urea binding format, a first sorbent layer can be loaded with at least one polymerizable urea complexing agent and a second sorbent layer can be loaded with at least one crosslinker. The first and/or second sorbent layer can be one or more layers. If more than one layer, the multiple layers can be the same or different from each other with respect to composition, amount, and/or other parameters. The loaded urea complexing agent can react with urea in dialysate passed through the first sorbent layer to form a soluble urea complex reaction product which thereafter travels with the dialysate out of the first sorbent layer and into the second sorbent layer. The crosslinker in the second sorbent layer can be crosslinkable with the soluble urea complex reaction product in the dialysate to form a cross-linked polymeric urea complex which is attached to the second sorbent layer. In the indicated single-stage urea binding format, an insolubilized crosslinked polymeric urea-bindable complex can be attached to a sorbent layer through which spent dialysate is passed. The complex can be formed, for example, by reacting a crosslinker loaded on a sorbent layer with a polymerizable urea complexing agent to form the insolubilized crosslinked polymeric urea-bindable complex attached to the sorbent layer. A direct urea sorbent can be obtained, for example, by a method of converting activated carbon to the sorbent through treatment with an effective urea complex agent, such as glyoxal, cross-linked by zirconium ions so that the zirconium glyoxal complex can be trapped within carbon pores or otherwise immobilized to the carbon. Urea-containing dialysate can be passed through the sorbent layer which has the insolubilized cross-linked polymeric urea-bindable complex attached thereto to complex urea therewith.

With respect to the pH conditions of these urea-binding sorbent reactions, low pH can be useful for the complexation of urea in dialysate with non-enzymatic urea complexing agents used in sorbent cartridges of the present invention. While not desiring to be bound to a theory, the stability of a urea complex formed with a non-urease urea complexing agent can benefit from the formation of a hydrogen bond, which benefits from a low pH. The low pH provided in this respect can be about 2 or less, or from about 0.1 to about 2, or from about 0.1 to about 1.8, or from about 0.5 to about 1.5, or other low pH values within these range values. The urease-free sorbents used in sorbent cartridges of the present invention can be acidified, such as acidified ZP (AZP), acidified carbon, and/or other acidified non-enzymatic sorbents. Regenerated dialysate that passes through these acidified sorbent materials can emerge with acidic pH. Acidified zirconium phosphate or AZP, for example, means the $H^+$ form of zirconium phosphate. AZP can have the composition, structures, and properties such as described in U.S. Patent Application Publication No. 2010/0078387 A1, which is incorporated in its entirety by reference herein. AZP can be prepared, for example, by following the methods disclosed in U.S. Pat. No. 6,818,196 and U.S. Patent Application Publication No. 2006/0140840 A1, which are incorporated in their entirety by reference herein. For example, AZP can be prepared by a reaction between aqueous solutions of a zirconium salt and phosphoric acid. The reaction can form a gelatinous precipitate that can be filtered and washed until excessive phosphoric acid is removed, and then dried in an oven, such as to a moisture level of from about 12 to 18 weight percent Loss on Drying (LOD). Alternatively, AZP can be prepared by heating zirconium oxychloride (ZOC) with soda ash to form sodium zirconium carbonate, and treating the sodium zirconium carbonate with caustic soda to form alkaline hydrous zirconium oxide. An aqueous slurry of the alkaline hydrous zirconium oxide can then be heated while adding phosphoric acid and an acid zirconium phosphate recovered. An aqueous slurry of the AZP can also be titrated with a basic agent, such as caustic soda, until a desired acidic pH is reached. Alternatively, AZP can be prepared by preparing a solution of zirconium oxychloride (ZOC) and an organic chemical additive in water, and then titrating with concentrated hydrochloric acid (HCl) to fully dissolve the precipitate. This ZOC solution can then be added to a solution of phosphoric acid to produce a slurry of AZP precipitate.

For column application and design, the acidity of the regenerated dialysate exiting from the urea binder column typically is removed before the dialysate is reused in a dialyzer. The acidity of the dialysate can be removed in the same or a different cartridge as where urea is complexed and removed, for example, by using at least one alkaline sorbent in the same cartridge as a back-up layer to the urea complexing and removal layer or layers. The alkaline sorbent used for this purpose can be, for example, alkaline HZO, alkaline ZP, and/or other alkaline sorbent layers. One or a plurality of the same or different types of these alkaline sorbent layers can be used in a cartridge. The alkaline sorbent, such as alkaline HZO and/or alkaline ZP, can be prepared, for example, by following the methods such as disclosed in U.S. Pat. Application Publication Nos. US 2010/0078387 A1 and US 2006/0140840 A1, which are incorporated in their entirety by reference herein. Alkaline hydrous zirconium oxide can be prepared, for example, by the reaction of a zirconium salt, for example, BZS, or its solution in water with an alkali metal (or alkali metal compound) at ambient temperature, to form a NaHZO precipitate. The NaHZO particles can be filtered and washed until the anions of the zirconium salt are completely removed, and then preferably air dried, or dried in an oven at mild temperature (e.g., 60° F. to less than 90° F.) to a moisture level, for instance, of from about 25-30 weight percent LOD or lower, to form a free-flowing powder. NaHZO can be prepared, for example, by adding an aqueous solution of ZOC, titrated with concentrated HCl, to an aqueous solution of caustic soda. The HCl addition can prevent excessive gelation during the precipitation process as well as to promote particle growth.

As indicated, very low pH (e.g., a pH about 2 or less) can be a useful factor in the design for the stability of the urea complex formation. Accordingly, the alkaline sorbents can be used downstream to neutralize the pH of dialysate in column designs in the present invention. Further, the alkaline sorbent used to neutralize the pH of the dialysate can prevent decomposition of bicarbonate in the dialysate as well as leakage of $Zr^-$ ions and phosphate from the column.

The column designs of the present invention, in general, can provide useful urea adsorption capacity and/or performance of dialysate regeneration without the need of any urease or other enzymatic materials for urea removal. In other words, the present invention, in part, includes enzyme-free sorbent cartridges and/or methods for purifying dialysate.

The sorbent designs of the present invention can reduce the complexity of conventional sorbent dialysis designs (both cartridge and system). These reductions in complexity can include, for example, reducing ammonia generation, reducing variations in sodium ($Na^+$) and/or bicarbonate ($HCO_3^-$) ion levels in dialysate which can occur by interaction of enzymatic hydrolysis products of urea (e.g., ammonium ($NH_4^+$) and carbonate ($CO_3^{+2}$)) with zirconium sorbent in conventional treatment of dialysate with urease, and/or correcting for high $pCO_2$ levels (partial pressure of carbon dioxide) in dialysate. Specifically, a sorbent cartridge can be used in a sorbent cartridge of the present invention for removing urea by zirconium-based or carbon-based sorbents for sorbent dialysis to produce uniform compositions of regenerated dialysate (e.g., $Na^+$ and $HCO_3^-$ levels), and/or improve the performance of the sorbent cartridge such as in terms of uremic toxin binding capacity. Further, as indicated, a significantly smaller volume of water can be needed in the dialysate (e.g., about 2 L instead of about 6 L used with urease-containing sorbent columns). Smaller volumes of water can be used with the sorbent cartridges of the present invention as more uniform (less variable) levels of sodium ($Na^+$) and/or bicarbonate ($HCO_3^-$) ions, for example, occur in the dialysate treated with sorbent cartridge designs of the present invention, than conventional urease-containing sorbent cartridge designs. The present invention can avoid the disadvantages of enzymatic hydrolysis of urea to ammonia carbonate and/or adsorption of the ammonia by a zirconium sorbent (e.g., sodium zirconium phosphate (NaZrP)) in exchange for release of sodium and hydrogen ions. The present invention can reduce variations in sodium and bicarbonate ion levels in the dialysate. Other advantages of the sorbent cartridges of the present invention can include the avoidance of the risk of ammonia leakage from the cartridge breakthrough or the need for monitoring for such leakage with an ammonia sensor.

A sorbent cartridge of the present invention can eliminate the indicated disadvantages by the indicated conversion of zirconium-based sorbent or carbon-based sorbent into a direct urea binder material without needing the presence of urease or other enzyme for urea removal. The sorbent cartridge of the present invention can eliminate and simultaneously serve to purify dialysate or water to make up dialysate by removing toxic ions (cations and/or anions) and organics from water. Furthermore, the method can enhance the therapeutic value of sorbent dialysis by improving the efficiency of removing uremic toxins in addition to urea, such as creatinine, phosphate, uric acid, toxic anions (e.g., oxalate, sulfate), beta-2-microglobulin, protein bound uremic toxins, or any combinations thereof. Other possible direct urea binders, e.g., macromolecular polymers with functional groups such as oxystarch or chitosan, which are not derived from zirconium sorbents or carbon through urea complex formation as indicated herein, may not have sufficient urea binding capacity for sorbent dialysis for therapeutic value.

Urea is generally inactive for adsorption by zirconium or carbon itself. The present invention relates in part to making zirconium sorbents or carbon active for urea adsorption. This can be done, for example, in the indicated two-stage urea binding format such as by first reacting urea (that is present in spent dialysate) with a complexing agent(s) preloaded on a sorbent column (e.g., HZO, carbon, ZP) to form a soluble urea-complex, such as through the formation of hydrogen bond or coupling with dialdehyde (e.g., glyoxal). The urea complex thus formed can then be cross-linked by zirconium ion loaded on a succeeding zirconium sorbent layer to form a large molecular weight urea-bound zirconium polymeric complex. For example, the mechanism can allow zirconium ions to cross-link the complexing agent that binds with the urea, but not the urea molecule by itself directly, which is then withheld by the zirconium sorbent.

As shown by Scheme A in FIG. 1, for example, the dialysate regeneration process 100, which includes urea removal, can comprise running spent (urea-containing) dialysate 111 through a cartridge or column 110. The spent dialysate 111 is passed through a sorbent layer 112 (e.g., carbon, hydrous zirconium oxide, ZrP) loaded with urea complexing agent (e.g., dialdehyde, dicarboxylic acid, carboxylic acid, starch, starch phosphate, orthophosphric acid) before layer 113. The soluble urea complex thus formed in this layer 112 can then be cross-linked by zirconium ions loaded on a zirconium sorbent in succeeding layer 113 (relative to forward fluid flow direction) to form a polymeric zirconium complex retained by the layer 113. The urea-N capacity achieved by this method can be, for example, greater than about 18 g urea-N/Kg ZrP, or greater than about 20 g urea-N/Kg ZrP, or greater than about 22 g urea-N/Kg ZrP, or greater than about 25 g urea-N/Kg ZrP, or from about 18-25 g urea-N/Kg ZrP, or other values. These urea-N capacity values can be improved further to reduce cost and enhance efficiency. Additional layers optionally can be included in the cartridge before, after, and/or between layers 112, 113, and/or 114.

With respect to the zirconium ions loaded on a zirconium sorbent, such as in layer 113, the layer can be loaded with zirconium cations by treatment of zirconium sorbent. A zirconium ion source can be prepared, for example, by soaking a zirconium sorbent in zirconium oxychloride (ZOC) solution, followed by filtration and drying to moist powder, for instance, at a moisture level of about 20%-30% LOD. The zirconium sorbent used for this treatment can be, for example, HZO.EDTA, NaHZO, HZO.Acetate, NaZP, AZP, or any combinations thereof. As an example, Zr ion loaded zirconium phosphate (ZP) can be prepared by dissolving about 25-35 gm ZOC solid in about 175-225 ml deionized water. With agitation, about 80-120 gm NaZP powder can be added to the indicated ZOC solution with continued stirring for about 20-40 minutes. Chloride can be removed with filtering and washing, and the filter cake can be dried to about 20%-30% LOD to obtain the Zr ion loaded ZP.

As shown by Scheme B in FIG. 1, for example, a dialysate regeneration process 101, which also includes urea removal, can comprise running spent (urea-containing) dialysate 121 through a cartridge or column 120. Cartridge 120 can comprise the indicated single-stage urea binding format wherein a polyaldehyde (e.g., glyoxal) can be immobilized by cross-linking the polyaldehyde with zirconium ions to form a zirconium polymeric polyaldehyde complex (e.g., a dialdehyde complex), which can then be bound by a carbon or zirconium sorbent (e.g., activated carbon, ZrP, HZO) in a sorbent layer 122. Spent dialysate 121 then can be passed through the layer 122 loaded with the insolubilized zirconium polymeric polyaldehyde complex. The insolubilized zirconium polyaldehyde polymeric complex can be used as a urea binder itself, without need of additional urea binding materials. Additional layers optionally can be included in the cartridge before, after, and/or between layers 122 and 123.

The urea complexing agent can be, for example, particulated carbon which is converted into an active urea sorbent, for example, by loading acidified carbon with glyoxal cross-linked by zirconium. The adsorption capacity of the treated carbon for urea can be high. The treated carbon can be combined with a suitable zirconium ion and glyoxal binding agent in a separate layer of the same or a subsequent sorbent cartridge to stabilize the zirconium glyoxal polymeric complex and prevent leakage of zirconium and glyoxal from the treated carbon.

With respect to the urea sorbent in Scheme B in FIG. 1, for example, activated carbon can be converted into a direct urea binding active material by immobilizing glyoxal as a urea complex agent to the carbon. To convert activated carbon to a urea binder, carbon can be treated with a solution containing Zr glyoxal complex at low pH (e.g., acidic pH, such as pH<3). The solution can be acidified by addition of a concentrated acid, such as concentrated HCl or other mineral or organic acids. The glyoxal can be cross linked with zirconium (Zr) ions to form a large zirconium cross-linked polymeric complex which can be trapped within carbon pores or otherwise immobilized to the carbon. The large molecular weight crosslinked Zr glyoxal complex can be formed and trapped within the carbon pores upon drying of the treated carbon. A characteristic of the Zr glyoxal complex is that the Zr ion does not take away the active sites of glyoxal as a coupling agent with urea unlike other complex reagents with glyoxal such as gelatin, polyvinyl alcohol and starch. Without the zirconium ion, the activated carbon has very low adsorption capacity for glyoxal and urea. Although not desiring to be bound to theory, cross-linked insolubilized Zr glyoxal complex trapped within the carbon pores may couple with urea in spent dialysate through the formation of hydrogen bonds thus allowing the treated carbon to be urea binding active. The treated carbon can be acid washed to remove excessive unbound zirconium ions and glyoxal, and mildly heated to provide a dry form which can be loaded into a cartridge or other sorbent holding device. The acid wash can be, for example, a dilute acid, such as dilute HCl or other mineral or organic acids. Most urea complex agents such as glyoxal itself are soluble in water and are not adsorbed by carbon. As indicated, the zirconium crosslinked glyoxal complex can be immobilized to activated carbon. The urea-binding carbon sorbent product can be in a form of an insolubilized particulate material. When the treated carbon contacts with urea in spent dialysate solution, the cross linked zirconium glyoxal polymeric complex of the treated carbon can bind with the urea, which then is captured by the treated carbon. The adsorption of the other nitrogenous uremic toxins by the carbon is not affected by the indicated treatment with zirconium cross-linked polymeric complex. Untreated activated carbon (i.e., without the indicated treatment with the zirconium cross-linked polymeric complex) is in general a suitable adsorbent for metabolized nitrogenous uremic toxins but has very poor urea adsorption capacity. The indicated urea binding carbon provides advantages for sorbent dialysis because activated carbon can be an adsorbent for protein metabolized uremic toxins in various molecular size ranges that would not also include urea without the indicated treatment.

When treated as indicated, the dried treated carbon becomes urea binding active and can attain urea adsorption capacity, such as up to about 50 g urea per kg treated carbon, e.g., from about 1 to about 50 g urea/kg treated carbon, or from about 5 to about 50 g urea/kg treated carbon, or from about 10 to about 50 g urea/kg treated carbon, or from about 25 to about 50 g urea/kg treated carbon, or from about 10 to about 40 g urea/kg treated carbon, or from about 15 to about 35 g urea/kg treated carbon or other capacity values, as measured in a column test by passing a dialysate containing urea through the column. The urea-binding carbons can avoid or reduce the indicated possible problems associated with sorbent dialysis that uses the enzyme urease to convert the urea to ammonium carbonate, in a safe and possibly cost-reducing manner. The resultant urea binding carbon can be combined with zirconium sorbents such as zirconium phosphate, hydrous zirconium oxide, sodium zirconium carbonate in the form of a sorbent dialysis cartridge for purifying tap water and making up dialysate solution in sorbent regenerative dialysis to remove various uremic toxins from the patient (urea, creatinine, uric acid, phosphate, potassium, calcium etc.). Since no ammonium carbonate is produced as in conventional sorbent dialysis cartridge using urease for the urea conversion, the regenerated dialysate is highly pure and uniform in composition allowing the dialysis system to be greatly simplified.

In Schemes A and B in FIG. 1, a pH neutralization layer 114 or 123, as applicable, can be included to neutralize the acidity of the dialysate that emerges from the urea complex sorbent layer 113 or 122, respectively. The pH neutralization layer can be, for example, alkaline HZO or other alkaline sorbent material.

Figure 2:
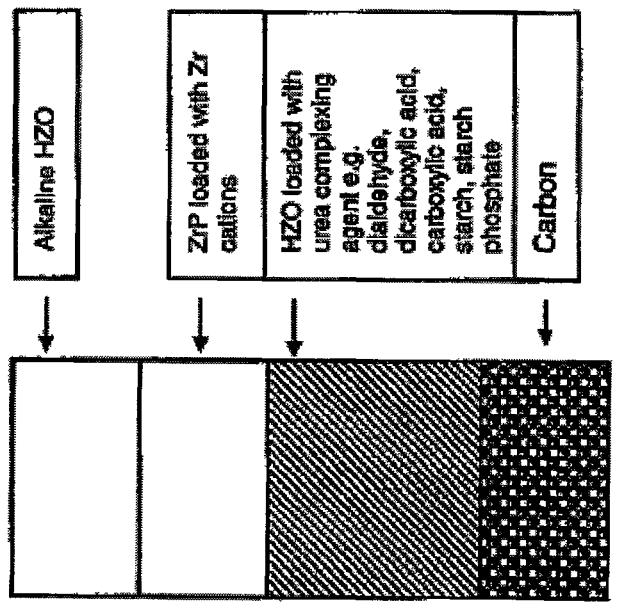
FIG. 2 is a schematic diagram of a sorbent cartridge according to an example of the present invention.
Figure 3:
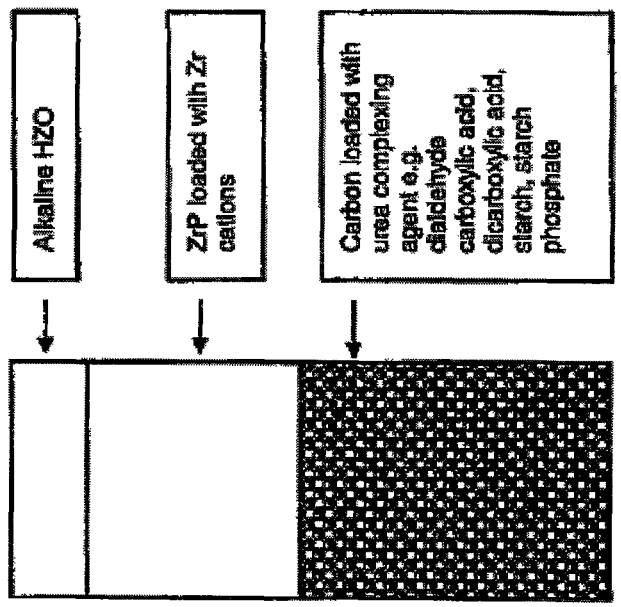
FIG. 3 is a schematic diagram of a sorbent cartridge according to an example of the present invention.
Figure 5:
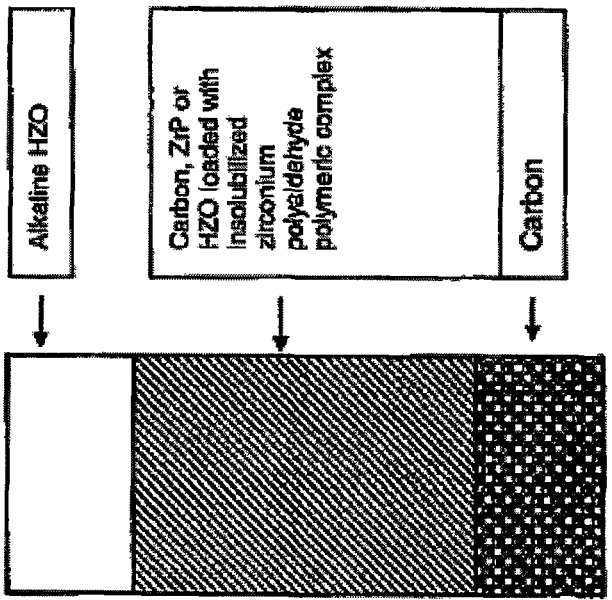
FIG. 5 is a schematic diagram of a sorbent cartridge according to an example of the present invention.
Figure 4:
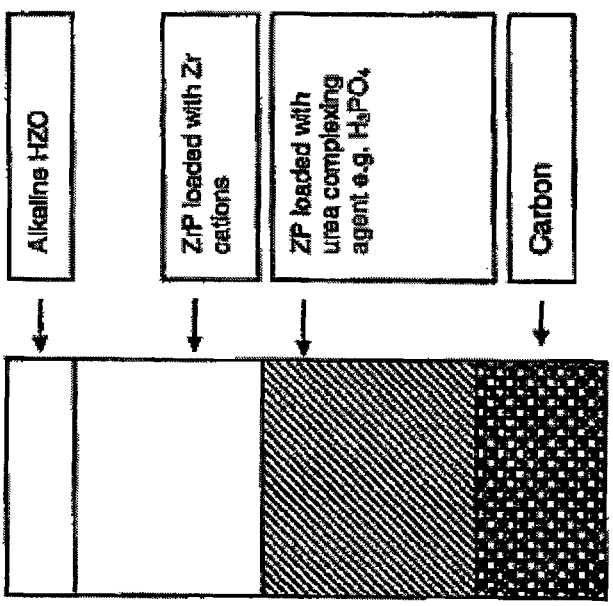
FIG. 4 is a schematic diagram of a sorbent cartridge according to an example of the present invention.

FIGS. 2, 3, and 4 show urea-complex-bindable columns which can be used, for example, in the indicated Scheme A shown in FIG. 1 of the present invention. In FIG. 2, the bottom or first layer is carbon (e.g., activated carbon or charcoal), the next layer can be HZO loaded with the urea complexing agent (e.g., dialdehyde, dicarboxylic acid, carboxylic acid, starch, starch phosphate), then ZrP loaded with cations, and then alkaline HZO. In FIG. 3, the design of layers used in the cartridge is similar to that of FIG. 1, where carbon is loaded with urea complexing agent, instead of HZO. In FIG. 4, the design of layers used in the cartridge is similar to that of FIG. 1 with a difference that the loaded urea complexing agent is different (e.g., phosphoric acid). FIG. 5 shows a urea complex-bindable column which can be used, for example, in the indicated Scheme B shown in FIG. 1 of the present invention. In FIG. 5, the bottom or first layer is carbon (e.g., activated carbon or charcoal), the next layer can be carbon, ZrP, or HZO loaded with insolublized zirconium polyaldehyde polymeric complex (the urea complexing agent), and then alkaline HZO.

Figure 6:
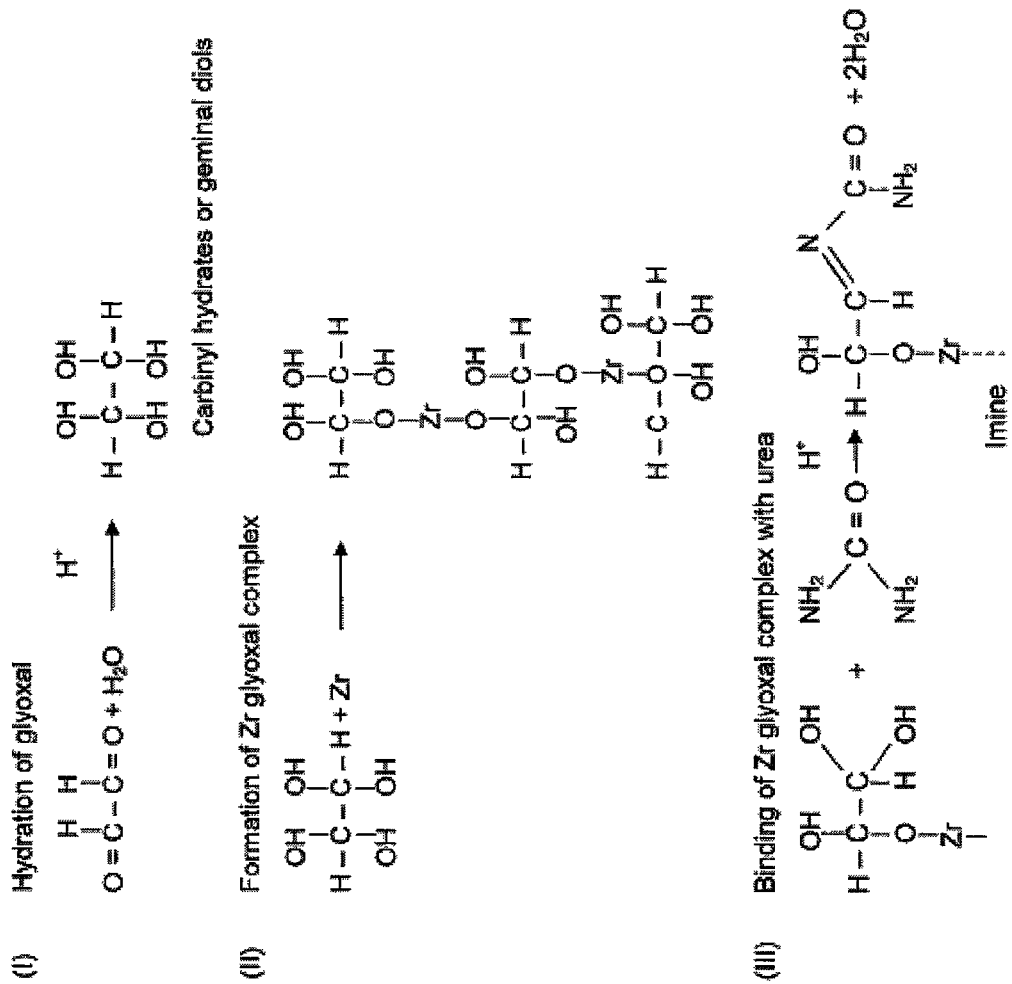
FIG. 6 shows reactions (I) and (II) for forming an insolubilized crosslinked polymeric urea-bindable complex), and reaction (III) of the binding of the complex with urea, according to examples of the present invention.

As shown in these illustrations, for example, the present invention, in part, relates to sorbent dialysis in the treatment of uremia which can be conducted by converting activated carbon to a direct urea binder by immobilizing cross-linked glyoxal onto the activated carbon using zirconium ion. The cartridge design for this sorbent dialysis is similar to the cartridge design shown for the Scheme B of FIG. 1 and in FIG. 5. A direct urea sorbent in this respect can be provided by converting activated carbon to the direct sorbent material through treatment of activated carbon or other particulated carbon material with an effective urea complexing agent, such as glyoxal or other polyaldehyde, which can be crosslinked by zirconium ion so that the zirconium glyoxal complex is immobilized on the carbon. Most urea complexing agents, such as glyoxal, are soluble in water and are not adsorbed by carbon. The formation of the zirconium glyoxal complex, such as by the reaction of hydrated glyoxal and zirconium ions, provides a complex that can be immobilized on the carbon. The treated carbon can then be acid washed to remove the excessive unbound zirconium ions and glyoxal, followed by mild heating, such as in an oven, to a dry form. The dried treated carbon then becomes urea binding active. The formation of the zirconium glyoxal complex and the binding of the complex with urea can be represented, for example, by reactions (I), (II), and (III) shown in FIG. 6. The urea binding active carbon can attain a urea adsorption capacity of at least about 10 g urea per kg treated carbon, or at least about 20 g urea per kg treated carbon, or at least about 30 g urea per kg treated carbon, or at least about 40 g urea per kg treated carbon, or up to about 50 g urea per kg treated carbon, or from about 10-50 g urea per kg treated carbon, or other values, as measured in a column test by passing a dialysate containing urea through the column.

The urea binding carbon typically is not used as the sole layer of a sorbent cartridge for therapies. As indicated with respect to Scheme B of FIG. 1, for example, the sorbent material of the single-stage urea binding format, such as the indicated urea binding carbon, is provided as an acidic sorbent and the acidity can be useful in the urea binding mechanism. Therefore, a pH neutralization layer can be included in a succeeding layer in the fluid flow direction within the cartridge of the urea binding carbon layer to neutralize the pH of the dialysate before exiting the cartridge. Alkaline hydrous zirconium sorbent (e.g., alkaline HZO), for example, can be used to back-up the urea binding carbon layer for this reason. In addition, leakage of unreacted zirconium ions, glyoxal unbound by carbon, or combinations of both from the urea binding carbon, can be prevented in sorbent cartridges of the present invention. It can be desirable to exclude glyoxal from column effluent which may be recirculated during dialysis. The complete or essentially complete removal of small amounts of glyoxal from dialysate that emerges from the urea binding carbon layer can be provided, for example, by including a succeeding layer of polyamine intercalated zirconium phosphate in the same cartridge (as the urea binding layer) to act as a glyoxal adsorbent to prevent glyoxal leakage from the cartridge. These deficiencies can be concurrently addressed by incorporating the urea binding carbon in a sorbent cartridge design which further employs an alkaline zirconium sorbent for pH neutralization in the dialysate and a layer of polyamine intercalated zirconium phosphate as a glyoxal adsorbent to prevent glyoxal leakage from the cartridge. These zirconium sorbents, other than removing the acidity and the leakage of zirconium and glyoxal from the urea-binding carbon, also can serve as sorbents to purify tap water used in making up the dialysate and/or to remove other uremic toxins from the patient, such as phosphate.

Polyamine intercalated zirconium phosphate can be prepared, for example, by adding acid zirconium phosphate to water with moderate agitation to form a slurry to which a polyalkylene polyamine, e.g., triethylene tetramine, can be slowly added. After the addition of polyalkylene polyamine is complete, the slurry can then be titrated from alkaline pH to about neutral 7, such by adding acid slowly to the slurry. The acid-titrated slurry can be heated to about 60° C. to about 85° C. and maintained at this temperature for several hours (e.g., about 3-5 hours). After heating, the slurry can be filtered and the resulting polyamine intercalated zirconium phosphate can be rinsed and air dried to form a free-flowing powder. Polyamine intercalated carbon, e.g., polyamine intercalated activated carbon, can be prepared in a similar manner, for example, without needing the acid titration step.

Figure 7:
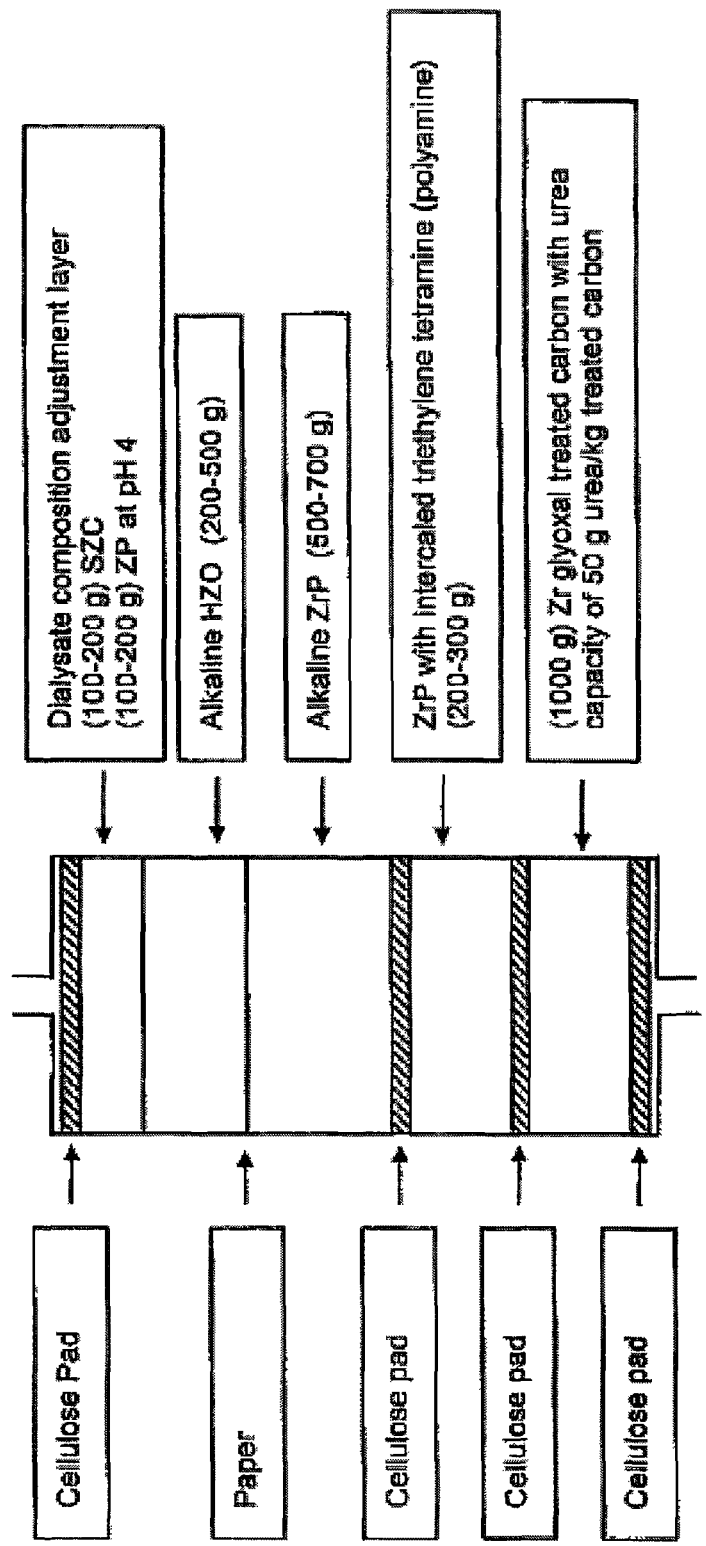
FIG. 7 is a schematic diagram of a sorbent cartridge according to an example of the present invention.
Figure 8A:
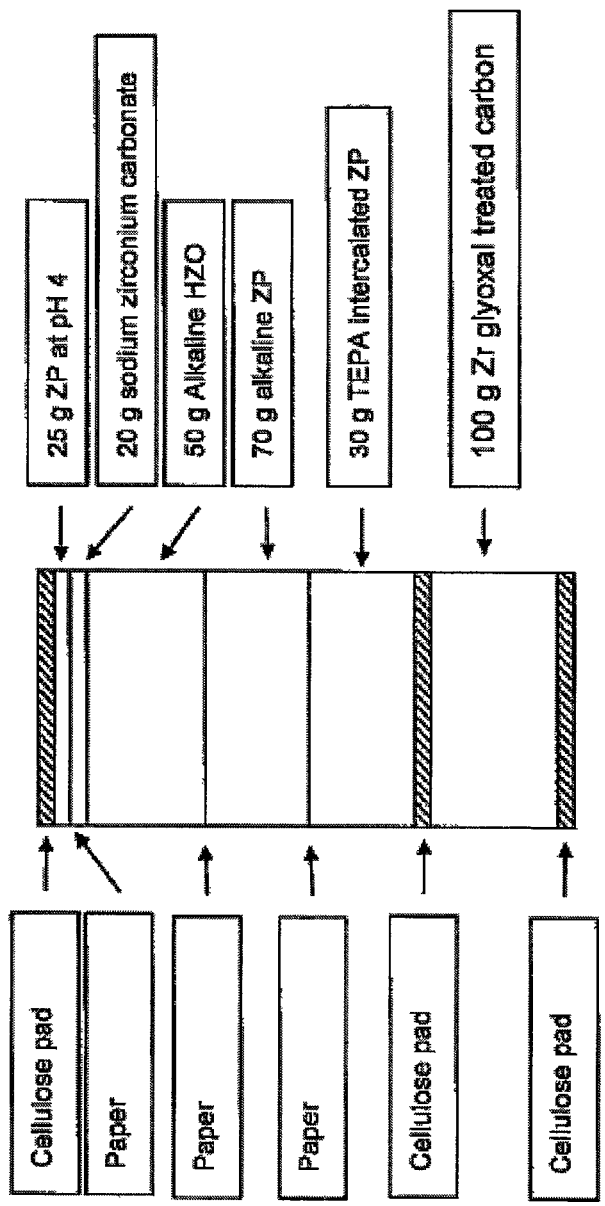
FIG. 8A is a schematic diagram of a sorbent cartridge according to an example of the present invention.

FIG. 7 shows a design of a sorbent cartridge that includes a urea-binding carbon layer which can have up to 50 g urea adsorption capacity per kilogram of carbon. FIG. 8A shows a non-limiting example of such a sorbent cartridge that includes a urea-binding carbon layer. The zirconium glyoxal treated carbon can be free from ammonium leakage as well as leakages of acetate, soluble Al and Zr, and also can be free from concanavalin from Jack Bean Meal. Uniform $Na^+$ and $HCO_3^-$ in dialysate can be provided throughout the treatment. Improvement of ANSI AAMI water quality for dialysate can be provided by complete removal of toxic anions (sulfate and $NO_3^-$), toxic metals and organics from tap water. The zirconium glyoxal treated carbon, which can have a urea binding capacity up to 50 g urea/kg carbon, can also serve as adsorbent for one or more of chlorine, creatinine, uric acid, a medium molecule such as β-2 microglobulin, bacteria, uremic toxins such as toxic anions (e.g. oxalate, citrate). A sorbent dialysis system using the zirconium glyoxal treated carbon can be simplified by reducing the volume of re-circulating dialysate, such as to 2 L or other volumes. Potential cost savings may be obtained due to replacement of zirconium sorbents with chemically treated carbon and elimination of urease. Minute unbound zirconium ions can be present in the urea binding carbon which can serve to form a polymeric complex with sulfate, nitrate, phosphate, organic solutes (e.g., oxygen containing organics), and biotoxins later absorbed by the alkaline HZO. Glyoxal present in the urea binding carbon can serve as disinfectant to remove bacteria and endotoxins, making the water ultrapure. The layer of zirconium phosphate (ZrP) with intercalated triethylene tetramine (polyamine) can serve to capture glyoxal effectively with a capacity, for example, of 44 mg/g at low pH to prevent any possible glyoxal leakage, and also can serve to form complexes with many metal ions that may be present in the dialysate, which are then absorbed by ZrP (e.g., chromium ion, copper ion). The alkaline ZrP can serve to neutralize acidity from the treated carbon, and also can serve to adsorb infusate cations $K^+$, $Ca^{2+}$, $Mg^{2+}$ as well as Zr ions and toxic trace metals and glyoxals. The alkaline HZO can serve to neutralize acidity from the treated carbon as indicated, and can also serve to adsorb toxic anions such as sulfate, phosphate, fatty acids, and other organics such as protein-bound toxins as well as glyoxal. The dialysate composition adjustment layers can include, for example, a small layer sodium zirconium carbonate and a small layer of ZP at pH 4 to adjust dialysate Na+, $HCO_3^-$, and pH.

Figure 8B:
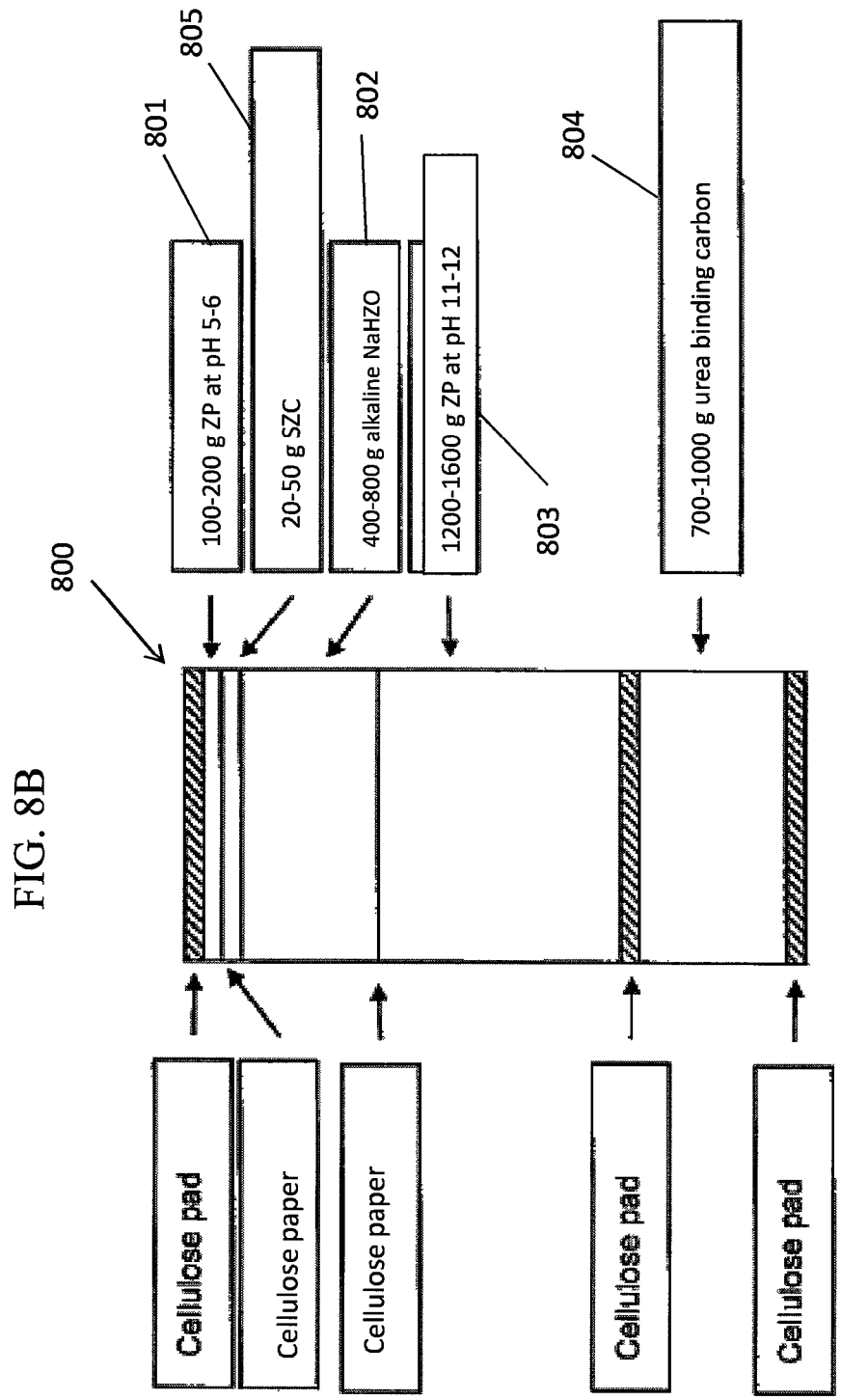
FIG. 8B is a schematic diagram of a sorbent cartridge according to an example of the present invention.

FIG. 8B shows another non-limiting example of a sorbent cartridge wherein urea binding carbon can be used for sorbent dialysis by incorporating the material in a cartridge design along with alkaline zirconium sorbents. In cartridge 800, the function of layer 801 can be to readjust the pH and bicarbonate level of the regenerated dialysate to physiological level as affected by the preceding alkaline zirconium sorbents NaHZO (layer 802) and ZP (layer 803). The function of the alkaline zirconium sorbent NaHZO (layer 802) can be to remove toxic anions (phosphate) and organics from the uremic patient and the tap water used to make dialysate (sulfate, nitrate). Layer 802 also can remove and prevent glyoxal leakage and acidity from the urea binding carbon (layer 804). The function of the alkaline ZP (layer 803) can be to remove $K^+$, $Ca^{2+}$, and $Mg^{2+}$ cations from a patient via the dialysate and toxic metals from tap water if used to make the dialysate. Layer 803 also can remove and prevent Zr and glyoxal leakage and acidity from the urea binding carbon (layer 804). The function of the urea binding carbon in layer 804 can be to remove urea, creatinine, uric acid and other nitrogenous uremic toxins from a patient via the dialysate and possible toxic organics from water used in preparing the dialysate. Layer 804 also can serve to disinfect the water, e.g., glyoxal is a disinfectant, and can remove bacteria and endotoxins from water as well as remove chlorine and chloramine. It is found that the urea binding capacity of the Zr glyoxal complex in layer 804 as well as the stability of the complex, can increase with the acidity of the treated carbon, and/or with the amount of glyoxal loaded on the carbon, and/or with a higher crosslinking molar ratio between Zr and glyoxal. It also is found that the alkaline zirconium sorbents can have high adsorption capacity for glyoxal to guard off leakage from the carbon provided that the alkalinity of the layers is not affected by the acid treated carbon, which means sufficient alkaline Zr sorbents are used in an example. Alternative designs of the cartridge to reduce the amount of alkaline zirconium sorbents can be made by using glyoxal adsorbents as back up support to prevent leakages such as carbon treated with gelatin solution, starch solution or polyvinyl alcohol solution. Also, anion exchange resins in the Off can be incorporated in the cartridge design to remove the acidity of the carbon allowing the enhancement of adsorption of glyoxal by Zr sorbents. The Zr glyoxal complex can also be immobilized on other inorganic sorbents instead of carbon to increase the urea binding capacity and the compact form of the urea binder, such as porous zirconium sorbents and silicates. Examples of amounts of each of the layers 801-805 of the cartridge 800 are indicated in FIG. 8B. Other amounts of any of these layers may be used. Additional cellulose pads and papers that can be optionally included in the cartridge 800 are also illustrated in of FIG. 8B.

Leakage of Zr and glyoxal from a sorbent cartridge using the urea binding carbon, such as illustrated in FIGS. 7, 8A, and 8B, can be reduced or prevented, for example, by inclusion in the cartridge of alkaline zirconium phosphate and alkaline zirconium oxide, both of which have high adsorption capacities for glyoxal and Zr. The alkaline sorbents can also neutralize the acidity of the acidified urea binding carbon and remove the uremic toxins as well as the toxic metals, toxic anions and organics from the tap water used to make up the dialysate. Carbon treated with polyvinyl alcohol solution, gelatin solution, or starch solution also may adsorb glyoxal through crosslinking reaction mechanism and prevent leakage of it from the cartridge. Carbon treated with polyvinyl alcohol also can be an excellent Zr adsorbent. Use of the anion exchange resin in the Off form also may neutralize the acidity of the urea binding carbon and hence reduce the amount of the use of alkaline zirconium sorbents. Also, a layer of zirconium sorbents containing a blend of ZrP (e.g., pH 5.5)/SZC used at the top of cartridge can serve for dialysate composition readjustment and make the $HCO_3^-$ and pH of the dialysate uniform throughout the treatment.

Evaluations of the sorbent cartridge incorporating the urease free urea-binding carbon, such as described in the examples herein, have shown advantages which remove or avoid shortcomings of sorbent cartridges for sorbent dialysis which use urease for urea binding. Ammonium ion toxicity concerns due to breakthrough or leakage of the cartridge are reduced or eliminated and the need for an ammonium ion sensor can be eliminated. Further, no adverse variation of $Na^+$ and $HCO_3^-$ ions in the dialysate throughout treatment are caused by the interaction of hydrolysis product of urea ($NH_4^+$ and carbonate converted by the enzymatic reaction of urease) and zirconium phosphate since there is no enzyme use in the design. Further, this can eliminate the necessity of accessories to adjust the dialysate composition (e.g., a K-SORB module, DI column, and the like). Further, there is no high $pCO_2$ in the dialysate as the pH of regenerated dialysate is consistently higher throughout treatment. The regenerated dialysate can reach ultrapure quality since immobilized glyoxal is a disinfectant to remove bacteria and endotoxins. Organics can be removed from the water used to make dialysate and organic toxins from patient fluid (e.g. phenol, fatty acid, and the like) due to zirconium ion complex formation followed by adsorption of these polymeric complexes, such as by HZO. Thus, urea binding sorbent can enhance the adsorption of varieties of toxic chemicals which are not able to be handled by conventional cartridges. Sulfate, nitrate and other anions can be removed from water used to make dialysate due to zirconium ion complex formation followed by adsorption of these polymeric complexes, such as by HZO. Thus, the sorbent cartridges having the urease-free urea binding sorbent of the present invention can enhance the capability of the sorbent cartridge to purify water in order to meet Association for the Advancement of Medical Instrumentation standards (AAMI standards). The capability to remove toxic metals from water can be enhanced with sorbent cartridges of the present invention for water purification to meet AAMI standards due to the high capacity of alkaline zirconium (e.g., ZrP) for cations and the binding of polyamine, for example, with metal ions to form chelates bound by zirconium sorbent (e.g., ZrP). The regenerated dialysate which is processed in sorbent cartridges of the present invention can be acetate free and aluminum free, such as due to the lack of HZO. acetate and alumina, which have been used in conventional cartridges.

The indicated two-stage or single-stage format urea binding materials, pH neutralization, and glyoxal adsorption materials of the present invention can be present as a layer (or layers) in sorbent cartridges. For the two-stage format urea binding materials, and depending on the application, for example, the first sorbent layer which comprises a polymerizable urea complexing agent loaded on carbon can be used in an amount, of from about 400 to about 1000 g per dialysis cartridge, such as from about 600 to about 1000 g per cartridge used in hemodialysis, or from about 400 to about 600 g per cartridge used in peritoneal dialysis. The second sorbent layer which comprises a crosslinker like AZP loaded with Zr ion can be used in an amount of from about 200 to about 800 g per dialysis cartridge, such as from about 400 to about 800 g per cartridge used in hemodialysis, or from about 200 to about 400 g per cartridge used in peritoneal dialysis. The pH neutralization layer or layers like alkaline ZP/alkaline HZO or SZC can be used in an amount of from about 200 to about 1800 g per cartridge, such as from about 500 to about 1500 g per cartridge (or other amounts above or below these ranges) used in hemodialysis, or from about 400 to about 800 g per cartridge (or other amounts above or below these ranges) used in peritoneal dialysis. For the single-stage format of urea binding material, and depending on the application, the sorbent layer which comprises an insolubilized crosslinked polymeric urea-bindable complex attached thereto can be used in an amount, for example, of from about 500 to about 2000 g per dialysis cartridge, such as from about 1000 to about 2000 g treated carbon per cartridge (or other amounts above or below these ranges) used in hemodialysis, or from about 750 to about 1250 g per cartridge (or other amounts above or below these ranges) used in peritoneal dialysis. The pH neutralization layer can be used in similar amounts as indicated for the cartridge having a two-stage format of urea binding material. The glyoxal adsorption material layer, if used, can be used in an amount, for example, of from about 100 to about 500 g per dialysis cartridge, such as from about 150 to about 400 g per cartridge used in hemodialysis, or from about 100 to about 200 g per cartridge used in peritoneal dialysis, or other amounts above or below these ranges.

Additional urease-free materials and layers optionally can be included in the same cartridge as the indicated two-stage or single-stage format urea binding material layers, pH neutralization material layer, and/or glyoxal adsorption material layer (if used). The optional additional layer(s), if used, preferably do not interfere with the indicated functions of the indicated two-stage or single-stage format urea binding materials, pH neutralization, and glyoxal adsorption materials (if used). Additional optional urease-free materials can include, for example, those described in U.S. Pat. No. 7,033,498 B2, U.S. Pat. No. 7,101,519 B2, and U.S. Pat. No. 6,878,283 B2, all incorporated in their entirety by reference herein. For example, various urease-free filter media sections within a tubular housing or cartridge can be used with the indicated two-stage or single-stage format urea binding material layers, pH neutralization material layer, and glyoxal adsorption material layer (if used) of the present invention. For dialysis, for example, a filter medium adapted to remove chlorine from tap water is preferred unless purified water is used as a base for the dialysate. The filter medium can be activated carbon. Activated carbon can also be used as a filter medium to bind heavy metals, oxidants, and chloramines. Alumina ($Al_2O_3$), activated carbon, anion-exchange resins, and diatomaceous earth can be used as adsorbents. The use of activated carbon to remove chlorine, if used, can precede the single-stage or two-stage urea binding material layers. Supplemental cation exchange materials can be used to bind ammonium, calcium, magnesium, potassium, and other cations as well as toxic trace metals in tap water. Such cation exchange materials can include AZP and/or ZrP. Anion exchange materials can bind phosphate, fluoride, and/or other heavy metals. Such anion exchange materials can include NaHZO. Cellulose filter pads, filter paper, and the like also can be included in the cartridge and can be used in conventional ways. As indicated, the optional additional layers preferably do not include, nor does the cartridge need to include (for adequate urea binding capacity) an immobilized enzyme layer for urea hydrolysis such as an immobilized urease layer.

A sorbent cartridge comprising a combination of two-stage or single-stage format of urea binding material layers and neutralization material layer as detailed above can be utilized to prepare purified dialysate for dialysis. The dialysate can comprise tap water. The sorbent cartridge can act as a dialysate purification system. Dialysate levels of bacteria and endotoxin can be maintained, for example, at <1 CFU/ml bacteria and <0.3 EU/ml endotoxin.

An apparatus for conducting dialysis can comprise a sorbent cartridge comprising a combination of two-stage or single-stage format urea binding material layer(s) and neutralization material layer(s) as detailed above, and a dialyzer in fluid communication with the sorbent cartridge, wherein spent dialysate passes from the dialyzer to and through the sorbent cartridge. The spent dialysate can be spent hemodialysate, spent peritoneal dialysate, or combinations thereof. The dialyzer can be in fluid communication with the blood of a patient.

A dialysis system can comprise a sorbent cartridge comprising a combination of two-stage or single-stage format urea binding material layer(s) and neutralization material layer(s) as detailed above, and a source of spent dialysate, wherein the source of the spent dialysate is in fluid communication with the sorbent cartridge and the spent dialysate passes to and through the sorbent cartridge. The spent dialysate can pass through the sorbent cartridge at a rate, for example, of from about 10 ml/min to about 1000 ml/min, from about 100 ml/min to about 550 ml/min, or from about 150 ml/min to about 400 ml/min, or other rates. The dialysis system can regenerate the spent dialysate, and can regenerate the spent dialysate to a pH level approximately equal to that of fresh dialysate. The system can also regenerate the spent dialysate without the formation of ammonia. The system can furthermore maintain a uniform level of $Na^+$, $HCO_3^-$ and pH while the spent dialysate is being regenerated.

Figure 9A:
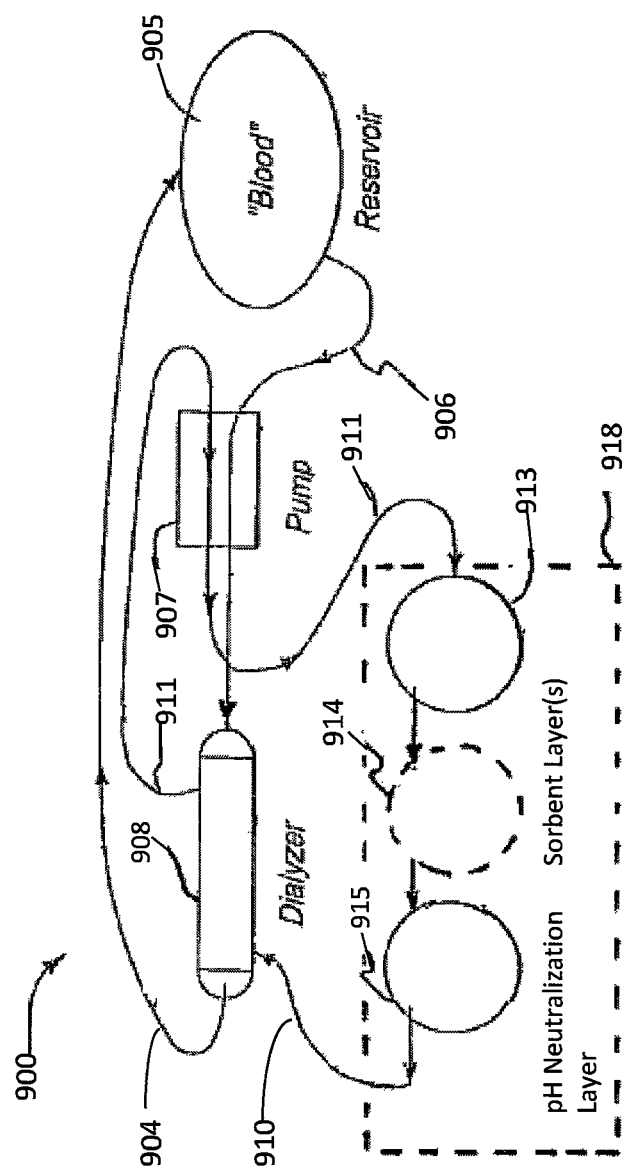
FIG. 9A shows a schematic illustration of a sorbent dialysis system according to an example of the present invention.

FIG. 9A shows a schematic illustration of a sorbent dialysis system 900 for performing dialysis according to an example of the present invention wherein a spent dialysate 911 containing at least urea or other complexable toxic anion or organic solute that is discharged from dialyzer 908 is passed through one or more sorbent layers 913 and 914. As indicated in the discussion of Schemes A and B of FIG. 1, for example, the urea complexing agent can be applied to removal of uremic toxins from dialysate in a two-stage urea binding format or a single-stage urea binding format. For a two-stage urea binding format, a first sorbent layer 913 can be loaded with a polymerizable urea complexing agent and a second sorbent layer 914 can be loaded with a crosslinker. The loaded urea complexing agent can react with urea in dialysate passed through the sorbent layer 913 to form a soluble urea complex reaction product which thereafter travels with the dialysate out of the sorbent layer 913 to sorbent layer 914 which contains a crosslinker which can be crosslinkable with the soluble urea complex reaction product in the dialysate to form a crosslinked polymeric urea complex which is attached to the sorbent layer 914. For a single-stage urea binding format, an insolubilized crosslinked polymeric urea-bindable complex instead can be attached to sorbent layer 913, and the sorbent layer 914 is not needed. The toxins in the spent dialysate 911 are removed in sorbent layer 913, or layers 913 and 914 if applicable, to provide dialysate free from or at least in reduced amount of toxic species than in the original spent dialysate 911. The pH neutralization layer 915 can comprise an alkaline sorbent (effective for neutralizing the acidity of the dialysate) through which the spent dialysate is passable and emerges from the sorbent column or columns to produce a regenerated dialysate 910 having reduced content of the toxin species than in the spent dialysate 911. The layers 913, 914 if present, and pH neutralization layer 915 can be arranged in a single sorbent cartridge or column 918, or separate sorbent cartridges, in fluid communication with the dialyzer 908 for recirculating at least a portion of the regenerated dialysate thereto. A pump 907 can be used to pump blood 906 from the blood reservoir 905, e.g., a patient, and to pump spent dialysate 911 to the layer 913 and layer 915 from there. Filtered blood 904 is circulated from the dialyzer 908 back to the reservoir 905. The system of FIG. 9A can be used, for example, to apply the methods of Scheme A or Scheme B in FIG. 1.

Figure 9B:
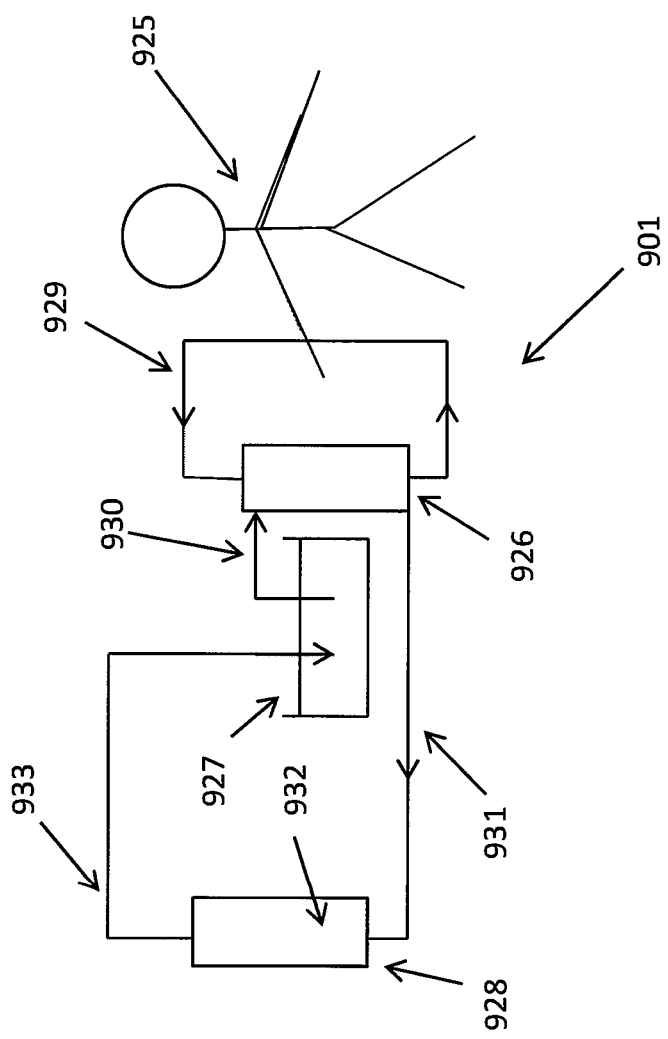
FIG. 9B shows a schematic illustration of a sorbent dialysis system according to an example of the present invention.

FIG. 9B shows a schematic illustration of a sorbent dialysis system 901 for performing dialysis according to an example of the present invention which includes a dialyzer 926 through which blood 929 drawn from a patient 925 passes on one side of a dialyzer membrane (not shown) and dialysate 930 passes on the other. The dialysate 930 is supplied from a dialysate reservoir 927. A urea binding carbon cartridge 928 receives spent dialysate 931 from the dialyzer 926, wherein the spent dialysate 931 which contains at least urea or other complexable toxic anion or organic solute that is discharged from dialyzer 926 is passed through a urea binding carbon layer 932 in the column. As indicated in the discussion of Scheme B of FIG. 1, for example, the urea complexing agent can be applied to removal of uremic toxins from dialysate in a single-stage urea binding format, which is illustrated in FIG. 9B. An insolubilized crosslinked polymeric urea-bindable complex on activated carbon, for example, can be used for the sorbent layer 932. As an example, column 928 can have the design of FIG. 8B. The toxins in the spent dialysate 931 are removed in sorbent layer 932 of column 928 to provide regenerated dialysate 933 which is free from or at least in reduced amount of toxic species than in the original spent dialysate 931. To simplify the figure, pumps, valves, and other process flow equipment that can be used with the system are not shown.

The present invention can be used to provide stationary sorbent dialysis systems or portable sorbent dialysis systems. The sorbent dialysis systems can include sorbent hemodialysis, a wearable artificial kidney, sorbent peritoneal dialysis, and other sorbent dialysis systems.

The present invention includes the following aspects/embodiments/features in any order and/or in any combination:

1. The present invention relates to a sorbent cartridge comprising at least one sorbent selected from:
(a) a first sorbent layer(s) loaded with at least one polymerizable urea complexing agent and a second sorbent layer(s) loaded with at least one crosslinker, wherein the crosslinker being crosslinkable with a soluble urea complex reaction product of the polymerizable urea complexing agent and urea when passing through the first sorbent layer, to form a crosslinked polymeric urea complex which is attachable to the second sorbent layer; and/or
(b) a sorbent layer(s) comprising an insolubilized crosslinked polymeric urea-bindable complex attached thereto, wherein the crosslinked polymeric urea-bindable complex comprising a reaction product of a crosslinker and polymerizable urea complexing agent.

2. The sorbent cartridge of any preceding or following embodiment/feature/aspect, wherein the cartridge is free of an immobilized urease layer, for instance, one that fluidly communicates with the first and second sorbent layers, or sorbent layer.

3. The sorbent cartridge of any preceding or following embodiment/feature/aspect, wherein total content of active urease in the cartridge is less than about 5 wt %, based on total immobilized weight portion of cartridge contents.

4. The sorbent cartridge of any preceding or following embodiment/feature/aspect, further comprising dialysate fluid at a pH of about 2 or less which communicates with sorbent (a) or sorbent (b).

5. The sorbent cartridge of any preceding or following embodiment/feature/aspect, wherein the sorbent cartridge comprises sorbent (a), wherein the polymerizable urea complexing agent is or comprises dialdehyde, dicarboxylic acid, monocarboxylic acid, starch, starch phosphate, orthophosphoric acid, or any combinations thereof, and the crosslinker is zirconium ions.

6. The sorbent cartridge of any preceding or following embodiment/feature/aspect, wherein the sorbent cartridge comprises sorbent (a), wherein the first sorbent layer is or comprises a hydrous zirconium oxide (HZO) layer, an activated carbon layer, a zirconium phosphate (ZrP) layer, or any combinations thereof.

7. The sorbent cartridge of any preceding or following embodiment/feature/aspect, wherein the second sorbent layer is or comprises a zirconium phosphate (ZrP) layer and the crosslinker is or comprises zirconium ions.

8. The sorbent cartridge of any preceding or following embodiment/feature/aspect, wherein the second sorbent layer is or comprises an acidic zirconium phosphate (AZrP) layer, and a layer that is or comprises an alkaline hydrous zirconium oxide layer is further included in the sorbent cartridge on a side of the AZrP layer opposite to the first sorbent layer.

9. The sorbent cartridge of any preceding or following embodiment/feature/aspect, wherein the sorbent cartridge has a urea-N capacity of greater than about 18 g urea-N/Kg ZrP.

10. The sorbent cartridge of any preceding or following embodiment/feature/aspect, wherein the sorbent cartridge comprises sorbent (b), wherein the sorbent layer is or comprises a hydrous zirconium oxide (HZO) layer, an activated carbon layer, a zirconium phosphate (ZrP) layer, or any combinations thereof.

11. The sorbent cartridge of any preceding or following embodiment/feature/aspect, wherein the complexing agent is or comprises dialdehyde, dicarboxylic acid, monocarboxylic acid, starch, starch phosphate, orthophosphoric acid, or any combinations thereof, and the crosslinker is or comprises zirconium ions.

12. The sorbent cartridge of any preceding or following embodiment/feature/aspect, further comprising an alkaline hydrous zirconium oxide layer.

13. The sorbent cartridge of any preceding or following embodiment/feature/aspect, wherein the complexing agent is or comprises glyoxal, the crosslinker is or comprises zirconium ions, and the insolubilized crosslinked polymeric urea-bindable complex is or comprises zirconium-crosslinked glyoxal complex.

14. The sorbent cartridge of any preceding or following embodiment/feature/aspect, further comprising a polyalkylenepolyamine intercalated ZrP layer, a polyalkylene imine intercalated ZrP layer, a polyalkylenepolyamine treated activated carbon layer, a polyalkylene imine treated activated carbon layer, or any combinations thereof.

15. The sorbent cartridge of any preceding or following embodiment/feature/aspect, further comprising an alkaline hydrous zirconium oxide layer.

16. The present invention is further directed to a method to regenerate or purify spent dialysate comprising passing the spent dialysate through the sorbent cartridge of any preceding or following embodiment/feature/aspect.

17. The present invention is further directed to a method of preparing purified fresh dialysate for dialysis comprising passing the dialysate through the sorbent cartridge of any preceding or following embodiment/feature/aspect.
18. The method of any preceding or following embodiment/feature/aspect, wherein the dialysate comprises tap water.
19. The present invention is further directed to a method of regenerating or purifying spent dialysate by a process selected from:
   (a) (i) passing urea-containing dialysate through a first sorbent layer loaded with a polymerizable urea complexing agent to form a soluble urea complex at a pH of about 2 or less,
      (ii) passing the soluble urea complex through a second sorbent layer loaded with a crosslinker which crosslinks with the soluble urea complex to form a crosslinked polymeric urea complex which is attached to the second sorbent layer; or
   (b) (i) reacting a crosslinker loaded on a sorbent layer with a polymerizable urea complexing agent to form an insolubilized crosslinked polymeric urea-bindable complex attached to the sorbent layer,
      (ii) passing urea-containing dialysate through the sorbent layer having the insolubilized crosslinked polymeric urea-bindable complex attached thereto to complex urea therewith (e.g., at a pH about 2 or less).
20. The method of any preceding or following embodiment/feature/aspect, wherein the cartridge is free of a urease layer through which the urea-containing dialysate or soluble urea complex passes.
21. The method of any preceding or following embodiment/feature/aspect, further comprising neutralizing the pH of the dialysate after passing through the second sorbent layer or the sorbent layer.
22. The present invention is further directed to an apparatus for conducting dialysis comprising a sorbent cartridge of any preceding or following embodiment/feature/aspect and a dialyzer in fluid communication with the sorbent cartridge, wherein spent dialysate passes from the dialyzer to and through the sorbent cartridge.
23. The apparatus of any preceding or following embodiment/feature/aspect, wherein the spent dialysate is spent hemodialysate, spent peritoneal dialysate, or combinations thereof.
24. The apparatus of any preceding or following embodiment/feature/aspect, wherein the dialyzer is in fluid communication with the blood of a patient.
25. The present invention is further directed to a dialysis system which comprises the sorbent cartridge of any preceding or following embodiment/feature/aspect, and a source of spent dialysate, wherein the source of the spent dialysate is in fluid communication with the sorbent cartridge and the spent dialysate passes to and through the sorbent cartridge.
26. The present invention is further directed to a method of making urea-binding carbon for sorbent devices, comprising:
a) combining glyoxal and a zirconium ion source solution to provide a glyoxal/zirconium solution;
b) immersing activated carbon in the glyoxal/zirconium solution including added acid to provide treated activated carbon;
c) separating solution from the treated activated carbon;
d) acid washing the treated activated carbon to provide acid-washed treated activated carbon; and
e) drying the acid-washed treated activated carbon to provide a urea-binding carbon product.
27. The present invention is further directed to a urea-binding carbon product of a process of any preceding or following embodiment/feature/aspect.

The present invention can include any combination of these various features or embodiments above and/or below as set forth in sentences and/or paragraphs. Any combination of disclosed features herein is considered part of the present invention and no limitation is intended with respect to combinable features.

The present invention will be further clarified by the following examples, which are intended to be only exemplary of the present invention. Unless indicated otherwise, all amounts, percentages, ratios and the like used herein are by weight.

EXAMPLES

Example 1

A zirconium glyoxal treated activated carbon for use as a direct urea binder was prepared in the following manner.

A solution of zirconium oxychloride solution was prepared by dissolving 100 g of the solid in 150 ml deionized water. 70 g of 40% glyoxal solution was added to the solution to form a homogeneous zirconium glyoxal complex solution by stirring. A 100 ml concentrate hydrochloric acid was added to the solution thereafter with continuous stirring until the resultant solution was clear. The solution was then transferred to an 800 ml beaker and 100 g of activated carbon was added to the beaker and immersed in the solution at room temperature for 4 hours. The residual solution was then removed by either decantation or filtration and the treated carbon was acid washed twice with a 250 ml diluted hydrochloric acid with acid strength of approximately 3.5 N, followed by decantation or filtration in each step. The solution-soaked carbon in the beaker was then dried in oven at mild temperature (approx. 100° F.) overnight to the completely dry form.

A 100 g treated carbon sample was tested alone (in a column) without other zirconium sorbents in a two inch diameter column by passing 2 L dialysate solution containing 120 mg % urea-N through the column at the flow rate 30 ml/min. The pH of the effluent was adjusted to neutral pH by adding NaOH. It was found that the urea in the column effluent was completely removed and the 100 g treated carbon column adsorbed greater than 5 g urea from the dialysate or greater than 50 g urea/kg treated carbon.

Example 2

An in-vitro test of a sorbent column incorporating urea-binding carbon was performed. The urea-binding carbon was made in a similar manner as in Example 1. In a first part (a) of the experiments, a single pass test for column effluent analysis was used. A two (2) inch diameter column of the configuration shown in FIG. 8A was prepared. A test bath composed of a 2.5 L dialysate solution was used, which had the composition and uremic toxin levels shown in Table 1.

TABLE 1

| | |
|---|---|
| $Na^+$ | 135 mEq/L |
| $HCO_3^-$ | 24 mEq/L |
| pH | 7.0 |
| Phosphate—P | 16.3 mg/dL |
| BUN | 101 mg/dL |

TABLE 1-continued

| | |
|---|---|
| Creatinine | 11.18 mg/dL |
| $K^+$ | 3.48 mEq/L |
| $Ca^{2+}$ | 3.99 mEq/L |
| $Mg^{2+}$ | 1.59 mEq/L |

The test solution was pumped through the indicated column at the flow rate of 10 ml/min, and column effluent samples were collected at 15 minutes, 30 minutes, 60 minutes, 120 minutes, 180 minutes, and 240 minutes for analysis of the electrolyte composition. Uremic toxins concentration was measured and the column was monitored for possible glyoxal and zirconium ion leakages. The column single pass effluent composition changes with respect to time for this experiment, are shown in Table 2.

TABLE 2

| Tests | To | 15 min | 30 min | 60 min | 120 min | 180 min | 240 min |
|---|---|---|---|---|---|---|---|
| $Na^+$ mEq/L | 135 | 132 | 132 | 133 | 136 | 135 | 134 |
| $HCO_3^-$ mEq/L | 25.8 | 25.4 | 25.2 | 25.0 | 25.0 | 25.3 | 25.5 |
| pH | 7.0 | 6.84 | 6.77 | 6.88 | 7.06 | 7.19 | 6.92 |
| BUN mg/dL | 3.1 | <DL | <DL | <DL | <DL | <DL | <DL |
| Creatinine mg/dL | <DL | <DL | <DL | <DL | <DL | <DL | <DL |
| $PO_4^-$-P mg/dL | <DL | <DL | <DL | <DL | <DL | <DL | <DL |
| $K^+$ mEq/L | <DL | <DL | <DL | <DL | <DL | <DL | <DL |
| $Ca^{2+}$ mEq/L | <DL | <DL | <DL | <DL | <DL | <DL | <DL |
| $Mg^{2+}$ mEq/L | <DL | <DL | <DL | <DL | <DL | <DL | <DL |
| Glyoxal leakage PPM | <DL | <DL | <DL | <DL | <DL | <DL | <DL |
| Zr leakage PPM | <DL | <DL | <DL | <DL | <DL | <DL | <DL |

The results, such as shown in Table 2, indicated $Na^+$, $HCO_3^-$ and pH in the column effluent were quite uniform throughout treatment (i.e., not affected by the column), while the $K^+$, $Ca^{2+}$, $Mg^{2+}$ as well as the uremic toxins BUN, creatinine and phosphate were completely removed in the column effluent. Furthermore, glyoxal and zirconium ion leakages were not detectable throughout the test.

The detection limits DL in Table 2 are summarized in Table 3 as follows.

TABLE 3

| | | | |
|---|---|---|---|
| DL for BUN | 2 mg/dL | DL for Ca | 0 mEq/L |
| DL for creatinine | 0.2 mg/dL | DL for Mg | 0.2 mEq/L |
| DL for $PO_4$—P | 0.5 mg/dL | DL for Glyoxal | 2.5 PPM |
| DL for K | 0.3 mEq/L | DL for Zr | 1 PPM |

In a second part (b) of these experiments, the column test in (a) was repeated with re-circulation of the column effluent to the bath. The bath composition change of this experiment simulates a patient in sorbent dialysis treatment. Table 4 shows re-circulation bath composition changes with respect to time for this experiment.

TABLE 4

| Tests | 0 min | 15 min | 30 min | 60 min | 120 min | 180 min | 240 min |
|---|---|---|---|---|---|---|---|
| $Na^+$ mEq/L | 135 | 134 | 133 | 135 | 137 | 134 | 135 |
| $HCO_3^-$ mEq/L | 24 | 25 | 25 | 24 | 24 | 24 | 25 |
| pH | 7.0 | 6.9 | 6.9 | 6.8 | 7.0 | 7.1 | 7.1 |
| BUN mg/dL | 101 | 89.2 | 72.8 | 56.4 | 32.7 | 19.7 | 2.9 |
| Creatinine mg/dL | 11.18 | 9.53 | 8.21 | 6.03 | 3.27 | 1.73 | <DL |
| $PO_4^-$-P | 16.3 | 14.45 | 12.4 | 9.32 | 5.13 | 2.71 | <DL |
| Glyoxal leakage detected PPM | <DL | <DL | <DL | <DL | <DL | <DL | <DL |
| Zr leakage detected PPM | <DL | <DL | <DL | <DL | <DL | <DL | <DL |

Example 3

Polyamine intercalated zirconium phosphate was prepared and then studied to observe its efficacy as a glyoxal adsorbent and as indicator of its ability to prevent glyoxal leakage in a column having urea binding carbon.

30 g of acid zirconium phosphate was added to 120 ml deionized water with moderate agitation. 60 g of triethylene tetramine was then slowly added to the slurry. After the addition was complete, the slurry was then titrated from pH 12 to about pH 7 by adding 70 ml concentrated HCl slowly to the slurry. The slurry was then heated to 80° C. and maintained at this temperature for 4 hours. After heating, the slurry was then vacuum filtered and the TETA intercalated ZrP filter cake was then rinsed with deionized water until no excessive or unbound polyamine was detected. The filter cake was then air-dried to form a free-flowing powder. The glyoxal adsorption capacity of the resulting powder (TETA intercalated ZrP) was determined in a 2 inch column by passing 2 L aqueous solution containing 1500 ppm glyoxal through the column at the flow rate 20 ml/min at a pH of 3 and the glyoxal concentration of the column effluent was determined. For comparison, glyoxal adsorption capacity was determined for two alkaline zirconium sorbents, which were an alkaline ZrP column and an alkaline HZO column, under similar experimental conditions. The experiments were repeated with the pH reduced to 3 for the alkaline sorbents. Table 5 shows the glyoxal adsorption test results of these experiments. The TETA intercalated ZrP provided robust glyoxal adsorption at the low pH values. The alkaline zirconium sorbents had unstable results depending on the pH, with adsorption capacity reduced to zero at pH3, and lower glyoxal adsorption for all the tested pH values for alkaline ZrP.

TABLE 5

| | |
|---|---|
| TETA intercalated ZrP | Glyoxal adsorption capacity 44 mg/g at pH 3 |
| Alkaline ZrP | Glyoxal adsorption capacity 30 mg/g, reduced to zero as ZP pH lowers to 3 |
| Alkaline HZO | Glyoxal adsorption capacity 65 mg/g, reduced to zero as ZP pH lowers to 3 |

Example 4

The removal of sulfate anion and copper metal ion for water purification to make dialysate was studied in this experiment. 2.5 L tap water containing 50 PPM sulfate and 20 PPM $Cu^{2+}$ (from 1000 PPM AA stock) was pumped through a 2 inch column containing a urea binding carbon similar to that described in Example 1 (FIG. 8A column) and tested for residual sulfate and $Cu^{2+}$ in the treated water (i.e., the column effluent). No sulfate ($SO_4^{+2}$) and copper ($Cu^{+2}$) were detected in the column effluent.

In additional experiments conducted on the removal of sulfate from water for water purification to make dialysate, the test was repeated by using 250 ppm sulfate in contaminated water to be treated by the column. It was found that the column was able to completely remove the sulfate so that the sulfate level in the column effluent was below the detection limit.

Example 5

The removal of uremic toxin and organics in addition to urea were studied in further evaluation of the therapeutic value of the urea binding carbon (FIG. 8A column). The uremic toxins and organics used in this experiment were phenol, a middle molecule such as β2-microglobulin, and protein bound uremic toxins such as indoxyl sulfate. Other than the uremic toxins used in this experiment, the test conditions were similar to that described in Example 2

Example 6

The adsorption of glyoxal by activated carbon loaded with polyamine was studied as an alternative method of removing glyoxal to the use of polyamine intercalated zirconium phosphate as shown in Example 3.

25 g triethylene tetramine TETA, as a polyamine, was mixed with 200 ml of deionized or reverse osmosis water by agitation. With continuous agitation at low speed, 50 g of activated carbon was added into the solution. After 1 hour of immersion in the solution at room temperature, the treated carbon was filtered by vacuum filtration and rinsed with 200 ml deionized or reverse osmosis water to remove the excess amine not adsorbed. The treated carbon was afterwards dried by mild heating (110° F.) in an oven to a dry form. The treated carbon sample was then tested in a 2 inch diameter column by passing a 2 L solution of glyoxal through the column with a concentration of the solution at 1 g glyoxal per L water. The amount of glyoxal adsorption by the column was calculated by analyzing the residual glyoxal in the column effluent after adsorption and found to be 2.72 g glyoxal on the basis of 25 g TETA/50 g carbon for the column.

The test was repeated by using 25 g of polyethylene imine PEI in 200 ml water as another polyamine solution to treat 100 g carbon. The treated carbon after drying was found to have adsorption capacity of 2.654 g glyoxal on basis of 25 g PEI/100 g carbon, which is about the same as the indicated TETA/carbon. After adsorption of glyoxal on the treated carbon loaded with polyamine TETA or PEI, it was found the carbon column also became urea binding active. By passing a 2 L of dialysate solution containing urea at the level of 100 mg urea-N through the column after glyoxal adsorption, it was found the urea-N adsorption capacity ranged from 0.32 g urea-N for the 25 g TETA/50 g carbon column to 1.8 g urea-N for the 25 gm PEI/100 g carbon column (where PEI is polyethylene imine). Therefore, these results show that the polyamine treated carbon can serve as additional urea binding material to the columns of Zr-glyoxal immobilized carbon as in Examples 1 and 2.

Example 7

A zirconium glyoxal treated activated carbon for use as a direct urea binder was prepared in the following manner.

A solution of zirconium oxychloride (ZOC) solution was prepared by dissolving 150 g of the solid in 300 ml deionized water or reverse osmosis purified water. 250 g of 40% glyoxal solution was added to the solution and mixed at room temperature. A 250 ml concentrated hydrochloric acid was added to the solution and mixed at room temperature to provide a Zr/glyoxal solution at reduced pH. 500 g of activated carbon was weighed in a tray and the Zr/glyoxal solution was completely poured into the tray. The carbon was immersed in the solution for two hours. The treated carbon was removed from the solution by using a filter funnel or plastic screen. The treated carbon was acid washed with 2 L dilute hydrochloric acid in the filter funnel or plastic screen. The treated carbon was dried at slightly elevated temperature (100° F.) in a corrosion proof dryer fitted with an acid vapor removal system or scrubber to yield 850 g urea-binding carbon (UBC).

Example 8

A test of a sorbent column incorporating urea-binding carbon was performed with a recirculation circuit set up having a 10 L bath containing spent dialysate of a composition and uremic toxin levels as shown in Table 6. Column effluent was recirculated to the bath during the experiment. The urea-binding carbon was made in a similar manner as in Example 7. A five (5) inch diameter urea-binding carbon cartridge of the configuration shown in FIG. 8B was prepared and used to regenerate the dialysate. The urea-binding carbon cartridge used 500 g urea binding carbon.

TABLE 6

| | |
|---|---|
| BUN | 118.9 mg/dL |
| Creatinine | 10.9 mg/dL |
| Phosphate—P | 12.31 mg/dL |
| $Na^+$ | 130 mEq/L |
| $HCO_3^-$ | 18.9 mEq/L |
| pH | 6.65 |
| $Cl^-$ | 110.9 mEq/L |
| $K^+$ | 3.16 mEq/L |
| $Mg^{2+}$ | 1.2 mEq/L |
| $Ca^{2+}$ | 3.76 mEq/L |

The test solution was recirculated through the indicated urea-binding carbon cartridge in the test circuit at the flow rate of 250 ml/minute. Table 7 shows re-circulation bath composition changes for this experiment with respect to time at different time increments (i.e., from 0 minutes (T0) to 360 min.). The bath composition change of this experiment simulates a patient in sorbent dialysis treatment. It is noted that the amount of urea removal estimated is 13.5 g per 500 g urea binding carbon used. $K^+$, $Ca^{2+}$ and $Mg^{2+}$ in the regenerated dialysate can be replenished by an infusion system after removal by cartridge.

TABLE 7

| Tests | T0 | 30 min | 60 min | 90 min | 120 min | 180 min | 240 min | 300 min | 360 min |
|---|---|---|---|---|---|---|---|---|---|
| BUN mg/dL | 118.9 | 85.6 | 72.4 | 66.6 | 64.3 | 59.6 | 57.7 | 57.1 | 55.8 |
| Creatinine mg/dL | 10.9 | 7.85 | 5.59 | 3.81 | 2.47 | 0.93 | 0.47 | 0.17 | 0.04 |
| $PO_4^-$-P mg/dL | 12.31 | 8.96 | 6.23 | 4.31 | 2.8 | 1.03 | 0.68 | 0.48 | 0.39 |
| $K^+$ mEq/L | 3.16 | — | — | — | — | — | — | — | 0.07 |
| $Mg^{2+}$ mEq/L | 1.2 | — | — | — | — | — | — | — | 0.06 |
| $Ca^{2+}$ mEq/L | 3.76 | — | — | — | — | — | — | — | 0.01 |
| $Na^+$ mEq/L | 130 | 134 | 139 | 141 | 145 | 147 | 143 | 144 | 145 |
| $HCO_3^-$ mEq/L | 18.9 | 16.5 | 14.7 | 14.6 | 15.6 | 15.7 | 16 | 16 | 16.6 |
| $Cl^-$ mEq/L | 110.9 | 105.2 | 109.5 | 111.7 | 113.9 | 114.7 | 107.3 | 107.9 | 108.4 |
| Zr leakage ppm | <DL | <DL | <DL | <DL | <DL | <DL | <DL | <DL | <DL |
| Glyoxal leakage ppm | <DL | <DL | <DL | <DL | <DL | <DL | <DL | <DL | <DL |

The data in Table 7 show a removal of BUN, creatinine, phosphate as well as $K^+$, $Ca^{2+}$ and $Mg^{2+}$ by the cartridge. Creatinine, phosphate, $K^+$, $Ca^{2+}$ and $Mg^{2+}$ are totally removed by the cartridge and are close to zero in the cartridge effluent. $Na^+$, bicarbonate and chloride in the effluent stay about the same concentration as in the bath. There is no detectable Zr and glyoxal in the cartridge effluent and in the bath. $Na^+$, $HCO_3^-$ levels and pH in the regenerated dialysate were close to uniformity during the treatment. It is noted that a small rise of $Na^+$ is expected due to ion exchange of $Na^+$ in ZP with $K^+$, $Ca^{2+}$ and $Mg^{2+}$. As other observations on the experiment, BUN level in cartridge effluent is about 30 mg/dL and can be reduced to zero by using more urea binding carbon in the cartridge.

Example 9

The prevention of glyoxal leakage using various sorbents was tested. The data was obtained by determining the equilibrium adsorption of glyoxal in a dialysate. The glyoxal concentration was measured by spectrophotometric analysis using Purpald reagent and wavelength of 400 nm with glyoxal standards in the range 0.2 ppm to 10 ppm. The measurement was made by plotting a calibration curve for glyoxal standards of absorbance versus ppm glyoxal. Dialysate of the same composition was used for each measurement. The adsorption capacity of glyoxal by the various tested sorbents are shown in Table 8.

TABLE 8

| Sorbent | pH | Glyoxal adsorption capacity (mg/g) |
|---|---|---|
| NaZrP | >10 | 30.6 |
| NaZrP | 7 | 15.8 |
| NaHZO | >10 | 65.02 |
| NaHZO | 7 | 32.4 |
| Carbon | 8 | 1.83 |
| Carbon | 5.3 | 1.42 |
| Carbon | 2 | 0.67 |
| Clay | 8 | 0 |
| Clay | 2 | 0.77 |
| TETA treated carbon | 11 | 108.8 |
| TETA treated carbon | 3 | 75.6 |
| PEI treated carbon | — | 106.16 |
| 40% cross-linked PEI blended with carbon | — | 48.6 |
| 40% cross-linked PEI | 1 | 46 |
| 40% cross-linked PEI | 7 | 86 |
| 10% cross-linked PEI | 1 | 56 |
| 10% cross-linked PEI | 7 | 158 |
| TETA treated ZP | 3 | 40 |

The carbon was additional carbon that was untreated (i.e., not UBC), which can be used in a cartridge as glyoxal adsorbent to prevent leakage from the cartridge. The test results indicate that while the activated carbon and clay have poor adsorption capacity for glyoxal, zirconium sorbents and sorbents (carbon, ZP, HZO, etc.) treated with polyamine have high adsorption capacity for glyoxal that can allow them to be used for prevention of glyoxal from leaking out the cartridge. The results further indicate that while the urea binding capacity of the urea binding carbon is in favor of acidity of the UBC which stabilizes the zirconium glyoxal complex trapped in carbon, the adsorption of glyoxal that leak out from the UBC is in favor of alkalinity of the sorbent. A feature of the design can be highly acidic UBC (resulted from adding concentrated HCL during the immersion of Zr glyoxal in carbon followed by acid washing), followed a backup layer of alkaline Zr sorbent to prevent glyoxal leakage.

Example 10

The urea binding carbon can be further treated to provide modified UBC by using Zr and glyoxal complex formation agents to eliminate Zr and glyoxal leakage from the UBC after acid wash. These reagents can consume the excess Zr and glyoxal by cross-linking reaction and prevent them from leaking out product at the sacrifice of some loss of urea binding capacity. For example, the UBC obtained after the acid wash in Example 7 can be further treated by dipping the UBC in acidified dilute aqueous solution of polyvinyl alcohol PVA, gelatin, starch or polyamine, followed by another acid wash and drying in oven. It has been found that UBC treated with PVA can reduce glyoxal leakage to 65 mg/Kg UBC and Zr leakage to 0.46 g/Kg UBC while maintaining urea adsorption capacity at 19.5 mg/g UBC. Furthermore, UBC treated with starch can reduce glyoxal leakage to 67.5 mg/Kg UBC while maintaining urea adsorption at 17 mg/g, and UBC treated with gelatin can reduce Zr leakage to 0.5 g/Kg with urea adsorption at 12.4 mg/g. Further, the reduced Zr and glyoxal leakages can be completely eliminated by using a small amount of alkaline zirconium sorbent back-up.

Example 11

The effect of pH control on a urea binding carbon cartridge was experimentally tested. It was found that the performance of the cartridge can be greatly improved and the amount of zirconium sorbents can be greatly reduced when the acidity (hydrogen ions) in dialysate derived from the UBC is removed by using a layer of ion exchange resin in the OH⁻ form. The improvement includes the control of sodium and bicarbonate in regenerated dialysate, and the reduction of Zr and glyoxal leakage from UBC to be removed by zirconium sorbents.

Applicant specifically incorporates the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

It will be apparent to those skilled in the art that various modifications and variations can be made to the embodiments of the present invention without departing from the spirit or scope of the present invention. Thus, it is intended that the present invention covers other modifications and variations of this invention provided they come within the scope of the appended claims and their equivalents.

What is claimed is:

1. A sorbent cartridge comprising sorbent which comprises at least one first sorbent layer loaded with at least one polymerizable urea complexing agent and at least one second sorbent layer loaded with at least one crosslinker wherein said crosslinker comprises zirconium, and wherein the zirconium being crosslinkable with a soluble urea complex reaction product of said polymerizable urea complexing agent and urea when passing through the first sorbent layer, to form a crosslinked polymeric urea complex which is attachable to said second sorbent layer.

2. The sorbent cartridge of claim 1, wherein the sorbent cartridge is free of an immobilized urease layer.

3. The sorbent cartridge of claim 1, wherein total content of active urease in the cartridge is less than about 5 wt %, based on total immobilized weight portion of cartridge contents.

4. The sorbent cartridge of claim 1, further comprising dialysate fluid at a pH of about 2 or less, which communicates with the sorbent.

5. The sorbent cartridge of claim 1, wherein the complexing agent comprises dialdehyde, dicarboxylic acid, monocarboxylic acid, starch, starch phosphate, orthophosphoric acid, or any combinations thereof.

6. The sorbent cartridge of claim 1, wherein said first sorbent layer is a hydrous zirconium oxide (HZO) layer, an activated carbon layer, a zirconium phosphate (ZrP) layer, or any combinations thereof.

7. The sorbent cartridge of claim 1, wherein said second sorbent layer comprises zirconium phosphate (ZrP) layer.

8. The sorbent cartridge of claim 7, wherein said second sorbent layer is an acidic zirconium phosphate (AZrP) layer, and an alkaline hydrous zirconium oxide layer is further included in the sorbent cartridge on a side of the AZrP layer opposite to said first sorbent layer.

9. The sorbent cartridge of claim 7, having a urea-N capacity of greater than about 18 g urea-N/Kg ZrP.

10. A method to regenerate or purify spent dialysate comprising passing the spent dialysate through the sorbent cartridge of claim 1.

11. A method of preparing purified fresh dialysate for dialysis comprising passing the dialysate through the sorbent cartridge of claim 1.

12. The method of claim 11, wherein the dialysate comprises tap water.

13. A method of regenerating or purifying spent dialysate by a process comprising:
(i) passing urea-containing dialysate through a first sorbent layer loaded with a polymerizable urea complexing agent to form a soluble urea complex at a pH of about 2 or less,
(ii) passing said soluble urea complex through a second sorbent layer loaded with a crosslinker which crosslinks with the soluble urea complex to form a crosslinked polymeric urea complex which is attached to said second sorbent layer, wherein said crosslinker comprises zirconium ions.

14. The method of claim 13, wherein said regenerating or purifying is in the absence of a urease layer.

15. The method of claim 13, further comprising neutralizing the pH of the dialysate after passing through the second sorbent layer.

16. An apparatus for conducting dialysis comprising the sorbent cartridge of claim 1, and a dialyzer in fluid communication with the sorbent cartridge, wherein spent dialysate passes from the dialyzer to and through the sorbent cartridge.

17. The apparatus of claim 16, wherein the spent dialysate is spent hemodialysate, spent peritoneal dialysate, or combinations thereof.

18. The apparatus of claim 16, wherein the dialyzer is in fluid communication with the blood of a patient.

19. A dialysis system comprising the sorbent cartridge of claim 1 and a source of spent dialysate, wherein the source of the spent dialysate is in fluid communication with the sorbent cartridge and the spent dialysate passes to and through the sorbent cartridge.

* * * * *